(12) United States Patent
Kruck et al.

(10) Patent No.: US 11,878,071 B2
(45) Date of Patent: Jan. 23, 2024

(54) PRODUCT FOR DYEING KERATINOUS MATERIAL, CONTAINING AMINOSILICONE, A CHROMOPHORIC COMPOUND, PRESERVATIVE AND A FATTY CONSTITUENT

(71) Applicant: Henkel AG & Co. KGaA, Duesseldorf (DE)

(72) Inventors: Constanze Kruck, Grevenbroich (DE); Sandra Hilbig, Bochum (DE); Daniela Kessler-Becker, Leverkusen (DE); Sofie Baumann, Remscheid (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 25 days.

(21) Appl. No.: 17/620,093

(22) PCT Filed: Jun. 2, 2020

(86) PCT No.: PCT/EP2020/065210
§ 371 (c)(1),
(2) Date: Dec. 16, 2021

(87) PCT Pub. No.: WO2020/254102
PCT Pub. Date: Dec. 24, 2020

(65) Prior Publication Data
US 2022/0378687 A1    Dec. 1, 2022

(30) Foreign Application Priority Data

Jun. 19, 2019  (DE) .................. 10 2019 208 904.6

(51) Int. Cl.
*A61Q 5/10*  (2006.01)
*A61K 8/898* (2006.01)
*A61K 8/34* (2006.01)
*A61K 8/39* (2006.01)

(52) U.S. Cl.
CPC .............. *A61K 8/898* (2013.01); *A61K 8/342* (2013.01); *A61K 8/347* (2013.01); *A61K 8/39* (2013.01); *A61Q 5/10* (2013.01); *A61K 2800/432* (2013.01); *A61K 2800/438* (2013.01); *A61K 2800/596* (2013.01)

(58) Field of Classification Search
CPC ........ A61K 8/898; A61K 8/342; A61K 8/347; A61K 8/39; A61K 2800/432; A61K 2800/438; A61K 2800/596; A61K 8/31; A61K 8/34; A61Q 5/10; A61Q 5/065
USPC .......................................................... 8/405
See application file for complete search history.

(56) References Cited

U.S. PATENT DOCUMENTS 8,088,179 B2   1/2012 Sasao et al.
2017/0172876 A1* 6/2017 Weser ................ A61Q 5/10

FOREIGN PATENT DOCUMENTS

| DE | 102015225361 A1 | 6/2017 | |
| DE | 102018222022 A1 * | 6/2020 | .............. A61Q 5/10 |
| DE | 102018222024 A1 * | 6/2020 | .............. A61Q 5/10 |
| EP | 1138317 A2 | 10/2001 | |
| EP | 1803434 A1 | 7/2007 | |
| WO | WO 2015018412 A2 * | 2/2015 | .............. A61Q 5/10 |
| WO | 2017108828 A1 | 6/2017 | |
| WO | WO 2017/108828 A1 * | 6/2017 | ............. A61Q 5/065 |

\* cited by examiner

*Primary Examiner* — Eisa B Elhilo
(74) *Attorney, Agent, or Firm* — Lorenz & Kopf, LLP

(57) ABSTRACT

An agent for dyeing keratinous material is provided. The agent includes (a1) at least one amino-functionalized silicone polymer and (a2) at least one color-imparting compound. Further, the agent includes (a3) at least one preservative and (a4) at least one fat component.

20 Claims, No Drawings

PRODUCT FOR DYEING KERATINOUS MATERIAL, CONTAINING AMINOSILICONE, A CHROMOPHORIC COMPOUND, PRESERVATIVE AND A FATTY CONSTITUENT

CROSS-REFERENCE TO RELATED APPLICATION

This application is a U.S. National-Stage entry under 35 U.S.C. § 371 based on International Application No. PCT/EP2020/065210, filed Jun. 2, 2020, which was published under PCT Article 21(2) and which claims priority to German Application No. 10 2019 208 904.6, filed Jun. 19, 2019, which are all hereby incorporated in their entirety by reference.

TECHNICAL FIELD

The subject of the present application is an agent for coloring keratinous material, in particular human hair, which contains at least one amino-functionalized silicone polymer (a1), at least one coloring compound (a2), at least one preservative (a3) and at least one fatty constituent (a4).

BACKGROUND

A second object of this application is a method for dyeing keratinous material, in particular human hair, wherein an agent of the first object of the invention is applied to the keratinous material, allowed to act and then washed out again with water.

Changing the shape and color of keratinous material, especially human hair, is an important area of modern cosmetics. To change the hair color, the expert knows various coloring systems depending on the coloring requirements. Oxidation dyes are usually used for permanent, intensive dyeing's with good fastness properties and good grey coverage. Such colorants contain oxidation dye precursors, so-called developer components and coupler components, which, under the influence of oxidizing agents such as hydrogen peroxide, form the actual dyes among themselves. Oxidation dyes are exemplified by very long-lasting dyeing results.

When direct dyes are used, ready-made dyes diffuse from the colorant into the hair fiber. Compared to oxidative hair dyeing, the dyeing's obtained with direct dyes have a shorter shelf life and quicker wash ability. Dyeing with direct dyes usually remain on the hair for a period of between 5 and 20 washes.

The use of color pigments is known for short-term color changes on the hair and/or skin. Color pigments are generally understood to be insoluble, coloring substances. These are present undissolved in the dye formulation in the form of small particles and are only deposited from the outside on the hair fibers and/or the skin surface. Therefore, they can usually be removed again without residue by a few washes with detergents containing surfactants. Various products of this type are available on the market under the name hair mascara.

If the user wants particularly long-lasting dyeing's, the use of oxidative dyes has so far been his only option. However, despite numerous optimization attempts, an unpleasant ammonia or amine odor cannot be completely avoided in oxidative hair dyeing. The hair damage still associated with the use of oxidative dyes also has a negative effect on the user's hair. A continuing challenge is therefore the search for alternative, high-performance dyeing processes.

It was the object of the present disclosure to provide a dyeing system having color intensities comparable to oxidative dyeing. However, the oxidation dye precursors normally used for this purpose should not be used. A technology was sought that would make it possible to fix the colorant compounds known from the prior art (such as pigments in particular) to the hair in an extremely durable manner. When using the agents in a dyeing process, particularly intensive dyeing results with good fastness properties should be achieved.

BRIEF SUMMARY

An agent for dyeing keratinous material is provided. The agent includes (a1) at least one amino-functionalized silicone polymer and (a2) at least one color-imparting compound. Further, the agent includes (a3) at least one preservative and (a4) at least one fat component.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Surprisingly, it has now been found that the problem can be excellently solved if keratinous materials, in particular hair, are colored with an agent containing at least one amino-functionalized silicone polymer (a1), at least one coloring compound (a2), at least one preservative (a3) and at least one fatty constituent (a4).

A first object of the present disclosure is an agent for coloring keratinous material, in particular human hair, containing determined weight ratios optimized with respect to each other.

(a1) at least one amino-functionalized silicone polymer, and
(a2) at least one color-imparting compound, and
(a3) at least one preservative and
(a4) at least one fat component.

In the course of the work carried out on the present disclosure, it has been surprisingly shown that the use of a preservative (a3) in an agent containing an amino silicone (a1), a coloring compound (a2) and a fatty component (a4) leads to an increase in color intensity when this agent is applied in a dyeing process on the keratinous material, on human hair.

Keratinic Material

Keratinous material includes hair, skin, nails (such as fingernails and/or toenails). Wool, furs and feathers also fall under the definition of keratinous material.

Preferably, keratinous material is understood to be human hair, human skin and human nails, especially fingernails and toenails. Keratinous material is understood to be human hair.

Coloring Agent

The term "coloring agent" is used in the context of the present disclosure for a coloring of the keratin material, of the hair, caused using coloring compounds, in particular pigments. In this coloring process, the pigments are deposited as coloring compounds in a particularly homogeneous, uniform and smooth film on the surface of the keratin material.

Amino-Functionalized Silicone Polymers (a1)

As the first ingredient (a1) essential to the invention, the composition contains at least one amino-functionalized silicone polymer. The amino-functionalized silicone polymer may alternatively be referred to as amino silicone or amodimethicone.

Silicone polymers are generally macromolecules with a molecular weight of at least 500 g/mol, preferably at least 1000 g/mol, more preferably at least 2500 g/mol, particularly preferably at least 5000 g/mol, which comprise repeating organic units.

The maximum molecular weight of the silicone polymer depends on the degree of polymerization (number of polymerized monomers) and the batch size and is partly determined by the polymerization method. For the purposes of the present disclosure, it is preferred if the maximum molecular weight of the silicone polymer is not more than 107 g/mol, preferably not more than 106 g/mol, and particularly preferably not more than 105 g/mol.

The silicone polymers comprise many Si—O repeating units, and the Si atoms may carry organic radicals such as alkyl groups or substituted alkyl groups. Alternatively, a silicone polymer is therefore also referred to as polydimethylsiloxane.

Corresponding to the high molecular weight of silicone polymers, these are based on more than 10 Si—O repeat units, preferably more than 50 Si—O repeat units, and more preferably more than 100 Si—O repeat units, most preferably more than 500 Si—O repeat units.

An amino-functionalized silicone polymer is understood to be a functionalized silicone that carries at least one structural unit with an amino group. Preferably, the amino-functionalized silicone polymer carries multiple structural units, each having at least one amino group. An amino group is understood to mean a primary amino group, a secondary amino group and a tertiary amino group. All these amino groups can be protonated in the acidic environment and are then present in their cationic form.

In principle, good effects could be obtained with amino-functionalized silicone polymers (a1) if they carry at least one primary, at least one secondary and/or at least one tertiary amino group. However, dyeing's with the best wash fastness were observed when an amino-functionalized silicone polymer (a1) was used in agent (a), which contains at least one secondary amino group.

In a very particularly preferred embodiment, a process as contemplated herein is exemplified in that the agent (a) comprises at least one amino-functionalized silicone polymer (a1) having at least one secondary amino group.

The secondary amino group(s) may be located at various positions on the amino-functionalized silicone polymer. Particularly good effects were found when an amino-functionalized silicone polymer (a1) was used that has at least one, preferably several, structural units of the formula (Si amino).

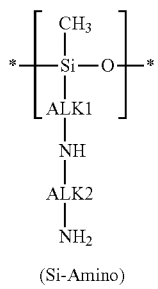

(Si-Amino)

In the structural units of the formula (Si-Amino), the abbreviations ALK1 and ALK2 independently represent a linear or branched, divalent $C_1$-$C_{20}$ alkylene group.

In another very particularly preferred embodiment, a process as contemplated herein is exemplified in that the agent (a) comprises at least one amino-functionalized silicone polymer (a1) comprising at least one structural unit of the formula (Si amino),

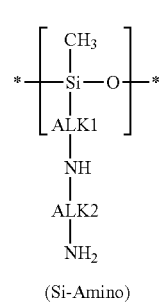

(Si-Amino)

where

ALK1 and ALK2 independently represent a linear or branched $C_1$-$C_{20}$ divalent alkylene group.

The positions marked with an asterisk (*) indicate the bond to further structural units of the silicone polymer. For example, the silicon atom adjacent to the star may be bonded to another oxygen atom, and the oxygen atom adjacent to the star may be bonded to another silicon atom or even to a $C_1$-$C_6$ alkyl group.

A divalent $C_1$-$C_{20}$ alkylene group can alternatively be referred to as a divalent or bivalent $C_1$-$C_{20}$ alkylene group, by which is meant that each ALK1 or AK2 grouping can form two bonds.

In the case of ALK1, one bond occurs from the silicon atom to the ALK1 grouping, and the second bond is between ALK1 and the secondary amino group.

In the case of ALK2, one bond is from the secondary amino group to the ALK2 grouping, and the second bond is between ALK2 and the primary amino group.

Examples of a linear divalent $C_1$-$C_{20}$ alkylene group include the methylene group (—$CH_2$—), the ethylene group (—$CH_2$—$CH_2$—), the propylene group (—$CH_2$—$CH_2$—$CH_2$—), and the butylene group (—$CH_2$—$CH_2$—$CH_2$—$CH_2$—). The propylene group (—$CH_2$—$CH_2$—$CH_2$—) is particularly preferred. From a chain length of 3 C atoms, divalent alkylene groups can also be branched. Examples of branched divalent $C_3$-$C_{20}$ alkylene groups are (—$CH_2$—CH($CH_3$)—) and (—$CH_2$—CH($CH_3$)—$CH_2$—).

In another particularly preferred embodiment, the structural units of the formula (Si amino) represent repeat units in the amino-functionalized silicone polymer (a1), so that the silicone polymer comprises multiple structural units of the formula (Si amino).

Particularly well-suited amino-functionalized silicone polymers (a1) with at least one secondary amino group are listed below.

Dyeing's with the very best wash fastnesses could be obtained if in the process as contemplated herein at least one agent (a) was applied to the keratinous material which contains at least one amino-functionalized silicone polymer (a1) comprising structural units of the formula (Si-I) and of the formula (Si-II)

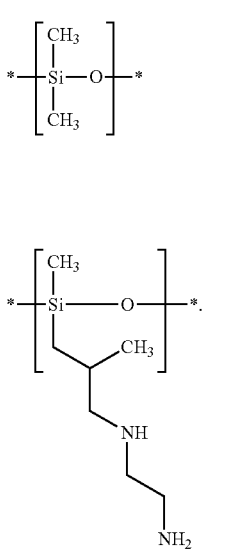

(Si-I)

(Si-II)

In a further explicitly quite particularly preferred embodiment, a process as contemplated herein is exemplified in that the agent (a) contains at least one amino-functionalized silicone polymer (a1) which comprises structural units of the formula (Si-I) and of the formula (Si-II)

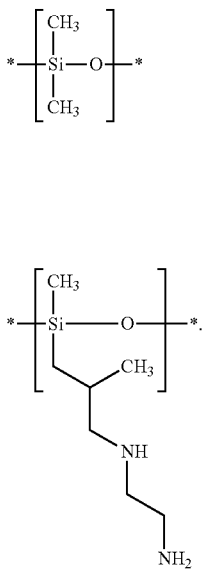

(Si-I)

(Si-II)

A corresponding amino functionalized silicone polymer with the structural units (Si-I) and (Si-II) is, for example, the commercial product DC 2-8566 or Dowsil 2-8566 Amino Fluid, which is commercially distributed by the Dow Chemical Company and bears the designation "Siloxanes and Silicones, 3-[(2-aminoethyl)amino]-2-methylpropyl Me, Di-Me-Siloxane" and the CAS number 106842-44-8.

In the context of a further preferred embodiment, a process as contemplated herein is exemplified by the application of an agent (a) to the keratinous material, the agent (a) comprising at least one amino-functional silicone polymer (a1) of the formula of formula (Si-III),

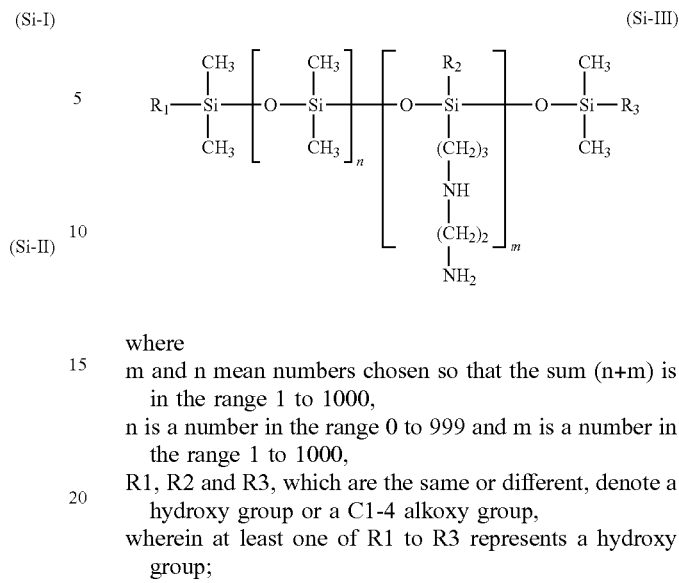

(Si-III)

where m and n mean numbers chosen so that the sum (n+m) is in the range 1 to 1000, n is a number in the range 0 to 999 and m is a number in the range 1 to 1000, R1, R2 and R3, which are the same or different, denote a hydroxy group or a C1-4 alkoxy group, wherein at least one of R1 to R3 represents a hydroxy group;

Further methods preferred as contemplated herein are exemplified by the application of an agent (a) to the keratinous material, the agent (a) comprising at least amino-functional silicone polymer (a1) of the formula of formula (Si-IV),

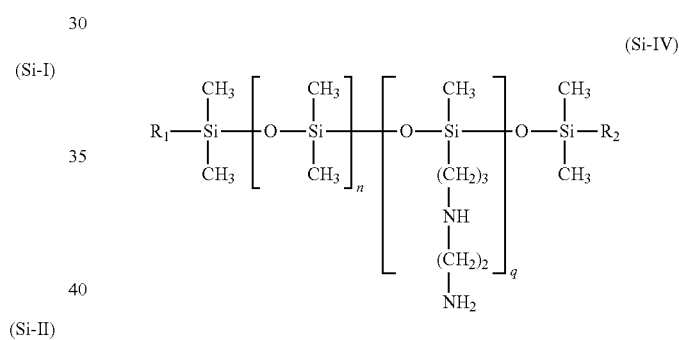

(Si-IV)

located in the p and q mean numbers chosen so that the sum (p+q) is in the range 1 to 1000, p is a number in the range 0 to 999 and q is a number in the range 1 to 1000, R1 and R2, which are different, denote a hydroxy group or a $C_1$-4 alkoxy group, at least one of R1 to R2 denoting a hydroxy group.

The silicones of the formulas (Si-III) and (Si-IV) differ in the grouping at the Si atom, which carries the nitrogen-containing group: In formula (Si-III), R2 represents a hydroxy group or a C1-4 alkoxy group, while the residue in formula (Si-IV) is a methyl group. The individual Si groupings, which are marked with the indices m and n or p and q, do not have to be present as blocks; rather, the individual units can also be present in a statistically distributed manner, i.e., in the formulas (Si-III) and (Si-IV), not every R1-Si (CH3)2 group is necessarily bonded to an —[O—Si(CH3)2] grouping.

Processes as contemplated herein in which an agent (a) containing at least one amino-functional silicone polymer (a1) of the formula of the formula (Si-V) is applied to the keratin fibers have also proved to be particularly effective with respect to the desired effects

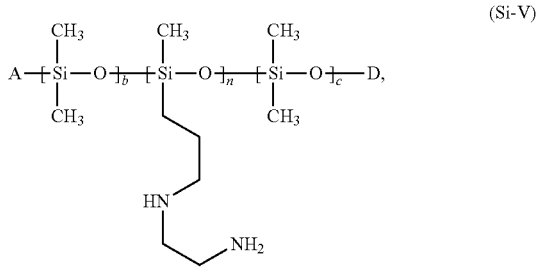

(Si-V)

located in the

A represents a group —OH, —O—Si(CH$_3$)$_3$, —O—Si(CH$_3$)$_2$OH, —O—Si(CH$_3$)$_2$OCH$_3$, D represents a group —H, —Si(CH$_3$)$_3$, —Si(CH$_3$)$_2$OH, —Si(CH$_3$)$_2$OCH$_3$, b, n and c stand for integers between 0 and 1000, with the specifications n>0 and b+c>0 at least one of the conditions A=—OH or D=—H is fulfilled.

In the above formula (Si-V), the individual siloxane units are statistically distributed with the indices b, c and n, i.e., they do not necessarily have to be block copolymers.

Agent (a) may further comprise one or more different amino-functionalized silicone polymers represented by the formula (Si-VI)

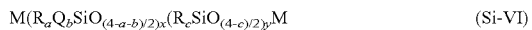

in which formula above R is a hydrocarbon or a hydrocarbon radical having from 1 to about 6 carbon atoms, Q is a polar radical of the general formula —R$^1$HZ wherein R$^1$ is a divalent linking group bonded to hydrogen and the radical Z composed of carbon and hydrogen atoms, carbon, hydrogen and oxygen atoms, or carbon, hydrogen and nitrogen atoms, and Z is an organic amino functional radical containing at least one amino functional group; "a" takes values ranging from about 0 to about 2, "b" takes values ranging from about 1 to about 3, "a"+"b" is less than or equal to 3, and "c" is a number ranging from about 1 to about 3, and x is a number ranging from 1 to about 2.000, preferably from about 3 to about 50 and most preferably from about 3 to about 25, and y is a number in the range of from about 20 to about 10,000, preferably from about 125 to about 10,000 and most preferably from about 150 to about 1,000, and M is a suitable silicone end group as known in the prior art, preferably trimethylsiloxy. Non-limiting examples of radicals represented by R include alkyl radicals, such as methyl, ethyl, propyl, isopropyl, isopropyl, butyl, isobutyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halohydrocarbon radicals, such as 3-chloropropyl, 4-bromobutyl, 3,3,3-trifluoropropyl, chlorocyclohexyl, bromophenyl, chlorophenyl and the like, and sulfur-containing radicals, such as mercaptoethyl, mercaptopropyl, mercaptohexyl, mercaptophenyl and the like; preferably R is an alkyl radical containing from 1 to about 6 carbon atoms, and most preferably R is methyl. Examples of R$^1$ include methylene, ethylene, propylene, hexamethylene, decamethylene, —CH$_2$CH(CH$_3$) CH$_2$—, phenylene, naphthylene, —CH$_2$CH$_2$SCH$_2$CH$_2$—, —CH$_2$CH$_2$OCH$_2$—, —OCH$_2$CH$_2$—, —OCH$_2$CH$_2$CH$_2$—, —CH$_2$CH(CH$_3$)C(O) OCH$_2$—, —(CH$_2$)$_3$CC(O)OCH$_2$CH$_2$—, —C$_6$H$_4$C$_6$H$_4$—, —C$_6$H$_4$CH$_2$C$_6$H$_4$—; and —(CH$_2$)$_3$C(O)SCH$_2$CH$_2$—.

Z is an organic amino functional residue containing at least one amino functional group. One possible formula for Z is NH(CH$_2$)$_z$NH$_2$, where z is 1 or more. Another possible formula for Z is —NH(CH$_2$)$_z$(CH$_2$)$_{zz}$NH, wherein both z and zz are independently 1 or more, this structure comprising diamino ring structures, such as piperazinyl. Z is most preferably an —NHCH$_2$CH$_2$NH$_2$ residue. Another possible formula for Z is —N(CH$_2$)$_z$(CH$_2$)$_{zz}$NX$_2$ or —NX$_2$, wherein each X of X$_2$ is independently selected from the group including hydrogen and alkyl groups having 1 to 12 carbon atoms, and zz is 0.

Q is most preferably a polar, amine-functional radical of the formula —CH$_2$CH$_2$CH$_2$NHCH$_2$CH$_2$NH 2. In the formulas, "a" takes values ranging from about 0 to about 2, "b" takes values ranging from about 2 to about 3, "a"+"b" is less than or equal to 3, and "c" is a number ranging from about 1 to about 3. The molar ratio of R$_a$Q$_b$ SiO$_{(4-a-b)/2}$ units to R$_c$SiO$_{(4-c)/2}$ units is in the range of about 1:2 to 1:65, preferably from about 1:5 to about 1:65 and most preferably by about 1:15 to about 1:20. If one or more silicones of the above formula are used, then the various variable substituents in the above formula may be different for the various silicone components present in the silicone mixture.

In a particularly preferred embodiment, a method as contemplated herein is exemplified by the application of an agent (a) to the keratinous material, wherein the agent (a) contains an amino-functional silicone polymer of formula (Si-VII)

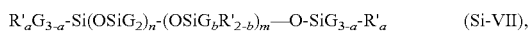

wherein means:

G is —H, a phenyl group, —OH, —O—CH$_3$, —CH$_3$, —O—CH$_2$CH$_3$, —CH$_2$CH$_3$, —O—CH$_2$CH$_2$CH$_3$, —CH$_2$CH$_2$CH$_3$, —O—CH(CH$_3$)$_2$, —CH(CH$_3$)$_2$, —O—CH$_2$CH$_2$CH$_2$CH$_3$, —CH$_2$CH$_2$CH$_2$CH$_3$, —O—CH$_2$CH(CH$_3$)$_2$, —CH$_2$CH(CH$_3$)$_2$, —O—CH(CH$_3$)CH$_2$CH$_3$, —CH(CH$_3$)CH$_2$CH$_3$, —O—C(CH$_3$)$_3$, —C(CH$_3$)$_3$;

a stands for a number between 0 and 3, especially 0;

b stands for a number between 0 and 1, especially 1, m and n are numbers whose sum (m+n) is between 1 and 2000, preferably between 50 and 150, where n preferably assumes values from 0 to 1999 and from 49 to 149 and m preferably assumes values from 1 to 2000, from 1 to 10, R' is a monovalent radical selected from

-Q-N(R")—CH$_2$—CH$_2$—N(R")$_2$

-Q-N(R")$_2$

-Q-N$^+$(R")$_3$A$^-$

-Q-N$^+$H(R")$_2$A$^-$

-Q-N$^+$H$_2$(R")A$^-$

-Q-N(R")—CH$_2$—CH$_2$—N$^+$R"H$_2$A$^-$, where each Q is a chemical bond, —CH$_2$—, —CH$_2$CH$_2$—, —CH$_2$CH$_2$CH$_2$—, —C(CH$_3$)$_2$—, —CH$_2$CH$_2$CH$_2$CH$_2$—, —CH$_2$C(CH$_3$)$_2$—, —CH(CH$_3$)CH$_2$CH$_2$—, R" represents identical or different radicals selected from the group including —H, -phenyl, -benzyl, —CH$_2$CH(CH$_3$)Ph, the C$_{1-20}$ alkyl radicals, preferably —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, —C(CH$_3$)$_3$, and A represents an anion preferably selected from chloride, bromide, iodide or methosulfate.

In the context of a further preferred embodiment, a process as contemplated herein is exemplified by the application of an agent (a) to the keratinous material, the agent (a) comprising at least one amino-functional silicone polymer (a1) of the formula (Si-VIIa),

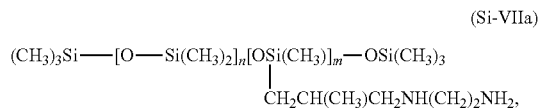

(Si-VIIa)

wherein m and n are numbers whose sum (m+n) is between 1 and 2000, preferably between 50 and 150, n preferably assuming values from 0 to 1999 and from 49 to 149, and m preferably assuming values from 1 to 2000, from 1 to 10.

According to the INCI declaration, these silicones are called trimethylsilylamodimethicones.

In another preferred embodiment, a method as contemplated herein is exemplified by the application of an agent (a) to the keratinous material, said agent (a) comprising at least one amino-functional silicone polymer of formula (Si-VIIb)

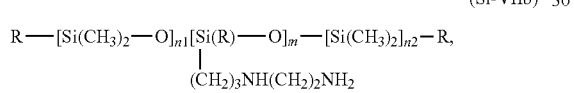

(Si-VIIb)

in which R represents —OH, —O—CH$_3$ or a —CH$_3$ group and m, n1 and n2 are numbers whose sum (m+n1+n2) is between 1 and 2000, preferably between 50 and 150, the sum (n1+n2) preferably assuming values from 0 to 1999 and from 49 to 149 and m preferably assuming values from 1 to 2000, from 1 to 10.

According to the INCI declaration, these amino-functionalized silicone polymers are called amodimethicones.

Regardless of which amino-functional silicones are used, agents (a) as contemplated herein are preferred which contain an amino-functional silicone polymer whose amine number is above 0.25 meq/g, preferably above 0.3 meq/g and above 0.4 meq/g. The amine number represents the milliequivalents of amine per gram of the amino-functional silicone. It can be determined by titration and also expressed in the unit mg KOH/g.

Furthermore, agents (a) which contained a special 4-morpholinomethyl-substituted silicone polymer (a1) are also suitable for use in the process as contemplated herein. This amino-functionalized silicone polymer comprises structural units of the formulae (SI-VIII) and of the formula (Si-IX)

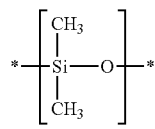

(Si-VIII)

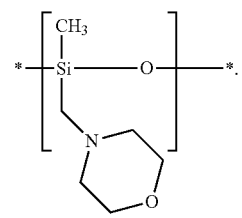

(Si-IX)

Corresponding 4-morpholinomethyl-substituted silicone polymers are described below.

A very particularly preferred amino-functionalized silicone polymer is known by the name of Amodimethicone/Morpholinomethyl Silsesquioxane Copolymer is known and commercially available from Wacker in the form of the raw material Belsil ADM 8301 E.

As a 4-morpholinomethyl-substituted silicone, for example, a silicone can be used which has structural units of the formulae (Si-VIII), (Si-IX) and (Si-X)

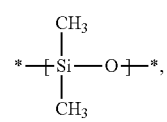

(Si-VIII)

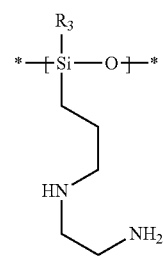

(Si-X)

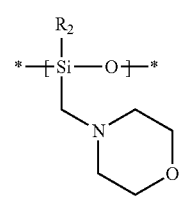

(Si-IX)

in which

R1 is —CH$_3$, —OH, —OCH$_3$, —O—CH$_2$CH$_3$, —O—CH$_2$CH$_2$CH$_3$, or —O—CH(CH$_3$)$_2$;

R2 is —CH$_3$, —OH, or —OCH$_3$.

Particularly preferred compositions (a) as contemplated herein contain at least one 4-morpholinomethyl-substituted silicone of the formula (Si-XI)

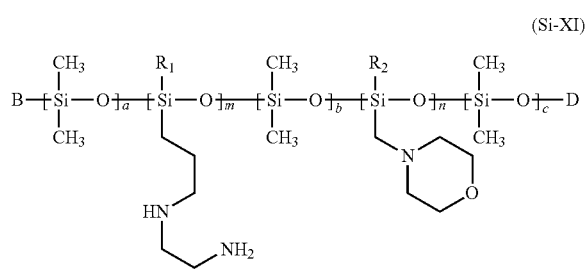

(Si-XI)

located in the

R1 is —CH$_3$, —OH, —OCH$_3$, —O—CH$_2$CH$_3$, —O—CH$_2$CH$_2$CH$_3$, or —O—CH(CH$_3$)$_2$;

R2 is —CH$_3$, —OH, or —OCH$_3$.

B represents a group —OH, —O—Si(CH$_3$)$_3$, —O—Si(CH$_3$)$_2$OH, —O—Si(CH$_3$)$_2$OCH$_3$, D represents a group —H, —Si(CH$_3$)$_3$, —Si(CH$_3$)$_2$OH, —Si(CH$_3$)$_2$OCH$_3$, a, b and c stand independently for integers between 0 and 1000, with the condition a+b+c>0 m and n independently of each other stand for integers between 1 and 1000 with the proviso that at least one of the conditions B=—OH or D=—H is fulfilled, the units a, b, c, m and n are distributed statistically or blockwise in the molecule.

Structural formula (Si-XI) is intended to illustrate that the siloxane groups n and m do not necessarily have to be directly bonded to a terminal grouping B or D, respectively. Rather, in preferred formulas (Si-VI) a>0 or b>0 and in particularly preferred formulas (Si-VI) a>0 and c>0, i.e., the terminal grouping B or D is preferably attached to a dimethylsiloxy grouping. Also, in formula (Si-VI), the siloxane units a, b, c, m and n are preferably statistically distributed.

The silicones used as contemplated herein represented by formula (Si-VI) can be trimethylsilyl-terminated (D or B=—Si(CH$_3$)$_3$), but they can also be dimethylsilylhydroxy-terminated on two sides or dimethylsilylhydroxy-terminated and dimethylsilylmethoxy-terminated on one side. Silicones particularly preferred in the context of the present disclosure are selected from silicones in which B=—O—Si(CH$_3$)$_2$OH and D=—Si(CH$_3$)$_3$
B=—O—Si(CH$_3$)$_2$OH and D=—Si(CH$_3$)$_2$OH
B=—O—Si(CH$_3$)$_2$OH and D=—Si(CH$_3$)$_2$OCH$_3$
B=—O—Si(CH$_3$)$_3$ and D=—Si(CH$_3$)$_2$OH
B=—O—Si(CH$_3$)$_2$OCH$_3$ and D=—Si(CH$_3$)$_2$OH to everyone. These silicones lead to exorbitant improvements in the hair properties of the hair treated with the agents of the invention, and to a seriously improved protection in oxidative treatment.

It has been found to be particularly advantageous if the agent as contemplated herein contains the amino-functionalized silicone polymer(s) (a1) in certain quantity ranges. Particularly good results were obtained when the agent contained—based on the total weight of the agent—a total amount of 0.1 to 8.0% by weight, preferably 0.2 to 5.0% by weight, more preferably 0.3 to 3.0% by weight, and most preferably 0.4 to 2.5% by weight.

In another particularly preferred embodiment, an agent as contemplated herein contains—based on the total weight of the agent—one or more amino-functionalized silicone polymers (a1) in a total amount of from 0.1 to 8.0% by weight, preferably from 0.2 to 5.0% by weight, more preferably from 0.3 to 3.0% by weight and very particularly preferably from 0.4 to 2.5% by weight.

Coloring Compounds (a2)

As a second essential component, the composition as contemplated herein contains at least one color-imparting compound (a2).

For the purposes of the invention, colorant compounds are substances capable of imparting a coloration to the keratin material. Particularly well-suited colorant compounds can be selected from the group of pigments, direct-acting dyes, photochromic dyes and thermochromic dyes.

In a further preferred embodiment, a composition as contemplated herein comprises at least one colorant compound (a2) from the group including pigments, direct dyes, photochromic dyes and thermochromic dyes.

Pigments within the meaning of the present disclosure are coloring compounds which have a solubility in water at 25° C. of less than 0.5 g/L, preferably less than 0.1 g/L, even more preferably less than 0.05 g/L. Water solubility can be determined, for example, by the method described below: 0.5 g of the pigment are weighed in a beaker. A stir-fish is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the possibly finely dispersed pigment, the mixture is filtered. If a proportion of undissolved pigments remains on the filter paper, the solubility of the pigment is below 0.5 g/L.

Suitable color pigments can be of inorganic and/or organic origin.

In a preferred embodiment, an agent as contemplated herein comprises at least one colorant compound (a2) from the group including inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-containing silicates, silicates, metal sulfides, complex metal cyanides, metal sulphates, chromates and/or molybdates. Preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, CI77510) and/or carmine (cochineal).

As contemplated herein, colored pearlescent pigments are also particularly preferred color pigments. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, mainly muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

In a further preferred embodiment, an agent as contemplated herein contains at least one colorant compound (a2) from the group of inorganic pigments, which is preferably selected from the group of colored metal oxides, metal hydroxides, metal oxide hydrates, silicates, metal sulfides, complex metal cyanides, metal sulfates, bronze pigments and/or from colored mica- or mica-based pigments coated with at least one metal oxide and/or a metal oxychloride.

In a further preferred embodiment, a composition as contemplated herein comprises (a) at least one colorant compound (a2) from the group of pigments selected from mica- or mica-based pigments which are reacted with one or more metal oxides from the group including titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Examples of particularly suitable color pigments are commercially available under the trade names Rona®, Coloron®, Xirona®, Dichrona® and Timiron® from Merck, Ariabel® and Unipure® from Sensient, Prestige® from Eckart Cosmetic Colors and Sunshine® from Sunstar.

Particularly preferred color pigments with the trade name Coloron® are, for example:

Coloron Copper, Merck, MICA, CI 77491 (IRON OXIDES)
Coloron Passion Orange, Merck, Mica, CI 77491 (Iron Oxides), Alumina
Coloron Patina Silver, Merck, MICA, CI 77499 (IRON OXIDES), CI 77891 (TITANIUM DIOXIDE)
Coloron RY, Merck, CI 77891 (TITANIUM DIOXIDE), MICA, CI 75470 (CARMINE)
Coloron Oriental Beige, Merck, MICA, CI 77891 (TITANIUM DIOXIDE), CI 77491 (IRON OXIDES)
Coloron Dark Blue, Merck, MICA, TITANIUM DIOXIDE, FERRIC FERROCYANIDE
Coloron Chameleon, Merck, CI 77491 (IRON OXIDES), MICA Coloron Aborigine Amber, Merck, MICA, CI 77499 (IRON OXIDES), CI 77891 (TITANIUM DIOXIDE)
Coloron Blackstar Blue, Merck, CI 77499 (IRON OXIDES), MICA
Coloron Patagonian Purple, Merck, MICA, CI 77491 (IRON OXIDES), CI 77891 (TITANIUM DIOXIDE), CI 77510 (FERRIC FERROCYANIDE)
Coloron Red Brown, Merck, MICA, CI 77491 (IRON OXIDES), CI 77891 (TITANIUM DIOXIDE)
Coloron Russet, Merck, CI 77491 (TITANIUM DIOXIDE), MICA, CI 77891 (IRON OXIDES)
Coloron Imperial Red, Merck, MICA, TITANIUM DIOXIDE (CI 77891), D&C RED NO. 30 (CI 73360)
Coloron Majestic Green, Merck, CI 77891 (TITANIUM DIOXIDE), MICA, CI 77288 (CHROMIUM OXIDE GREENS)
Coloron Light Blue, Merck, MICA, TITANIUM DIOXIDE (CI 77891), FERRIC FERROCYANIDE (CI 77510)
Coloron Red Gold, Merck, MICA, CI 77891 (TITANIUM DIOXIDE), CI 77491 (IRON OXIDES)
Coloron Gold Plus MP 25, Merck, MICA, TITANIUM DIOXIDE (CI 77891), IRON OXIDES (CI 77491)
Coloron Carmine Red, Merck, MICA, TITANIUM DIOXIDE, CARMINE
Coloron Blackstar Green, Merck, MICA, CI 77499 (IRON OXIDES)
Coloron Bordeaux, Merck, MICA, CI 77491 (IRON OXIDES)
Coloron Bronze, Merck, MICA, CI 77491 (IRON OXIDES)
Coloron Bronze Fine, Merck, MICA, CI 77491 (IRON OXIDES)
Coloron Fine Gold MP 20, Merck, MICA, CI 77891 (TITANIUM DIOXIDE), CI 77491 (IRON OXIDES)
Coloron Sienna Fine, Merck, CI 77491 (IRON OXIDES), MICA
Coloron Sienna, Merck, MICA, CI 77491 (IRON OXIDES)
Coloron Precious Gold, Merck, Mica, CI 77891 (Titanium dioxide), Silica, CI 77491 (Iron oxides), Tin oxide
Coloron Sun Gold Sparkle MP 29, Merck, MICA, TITANIUM DIOXIDE, IRON OXIDES, MICA, CI 77891, CI 77491 (EU)
Coloron Mica Black, Merck, CI 77499 (Iron oxides), Mica, CI 77891 (Titanium dioxide)
Coloron Bright Gold, Merck, Mica, CI 77891 (Titanium dioxide), CI 77491 (Iron oxides)
Coloron Blackstar Gold, Merck, MICA, CI 77499 (IRON OXIDES)

Other particularly preferred color pigments with the trade name Xirona® are for example:

Xirona Golden Sky, Merck, Silica, CI 77891 (Titanium Dioxide), Tin Oxide
Xirona Caribbean Blue, Merck, Mica, CI 77891 (Titanium Dioxide), Silica, Tin Oxide
Xirona Kiwi Rose, Merck, Silica, CI 77891 (Titanium Dioxide), Tin Oxide
Xirona Magic Mauve, Merck, Silica, CI 77891 (Titanium Dioxide), Tin Oxide.

In addition, particularly preferred color pigments with the trade name Unipure® are for example:

Unipure Red LC 381 EM, Sensient CI 77491 (Iron Oxides), Silica
Unipure Black LC 989 EM, Sensient, CI 77499 (Iron Oxides), Silica
Unipure Yellow LC 182 EM, Sensient, CI 77492 (Iron Oxides), Silica In a further embodiment, the composition as contemplated herein may also comprise one or more colorant compounds (a2) selected from the group including organic pigments The organic pigments as contemplated herein are correspondingly insoluble, organic dyes or color lacquers, which may be selected, for example, from the group of nitroso, nitro-azo, xanthene, anthraquinone, isoindolinone, isoindolinone, quinacridone, perinone, perylene, diketo-pyrrolo-pyrrole, indigo, thioindido, dioxazine and/or triarylmethane compounds.

Examples of particularly suitable organic pigments are carmine, quinacridone, phthalocyanine, sorghum, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In another particularly preferred embodiment, a composition as contemplated herein comprises at least one colorant compound (a2) from the group of organic pigments which is preferably selected from the group including carmine, quinacridone, phthalocyanine, sorghum, blue pigments having the color index numbers CI 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a color paint. As contemplated herein, the term color lacquer means particles comprising a layer of absorbed dyes, the unit of particle and dye being insoluble under the above mentioned conditions. The particles can, for example, be inorganic substrates, which can be aluminum, silica, calcium borosilate, calcium aluminum borosilicate or even aluminum.

For example, alizarin color varnish can be used.

Due to their excellent light and temperature resistance, the use of the above pigments in the agent (a) of the process as contemplated herein is particularly preferred. It is also preferred if the pigments used have a certain particle size. As contemplated herein, it is therefore advantageous if the at least one pigment has an average particle size $D_{50}$ of 1.0 to 50 μm, preferably 5.0 to 45 μm, preferably 10 to 40 μm, 14 to 30 μm. The mean particle size $D_{50}$, for example, can be determined using dynamic light scattering (DLS).

The colorant compounds (a2), the colorant compounds from the group of pigments, represent the second essential of the agent as contemplated herein and are preferably used in the agent in certain ranges of amounts.

Particularly good results were obtained when the agent contained—based on the total weight of the agent—one or more pigments (a2) in a total amount of 0.01 to 10.0% by weight, preferably 0.1 to 5.0% by weight, further preferably 0.2 to 2.5% by weight and very preferably 0.25 to 1.5% by weight.

In another very particularly preferred embodiment, an agent as contemplated herein is exemplified in that the agent contains—based on the total weight of the agent—one or more pigments (a2) in a total amount of from 0.01 to 10.0% by weight, preferably from 0.1 to 5.0% by weight, more preferably from 0.2 to 2.5% by weight and very particularly preferably from 0.25 to 1.5% by weight.

As colorant compounds (a2), the compositions as contemplated herein may also contain one or more direct dyes. Direct-acting dyes are dyes that draw directly onto the hair and do not require an oxidative process to form the color. Direct dyes are usually nitrophenylene diamines, nitroaminophenols, azo dyes, anthraquinones, triarylmethane dyes or indophenols.

The direct dyes within the meaning of the present disclosure have a solubility in water (760 mmHg) at 25° C. of more than 0.5 g/L and are therefore not to be regarded as pigments. Preferably the direct dyes within the meaning of the present disclosure have a solubility in water (760 mmHg) at 25° C. of more than 1.0 g/L.

Direct dyes can be divided into anionic, cationic and non-ionic direct dyes.

In a further embodiment, a process as contemplated herein is exemplified in that the agent (a) comprises at least one colorant compound (a2) from the group including anionic, non-ionic and cationic direct dyes.

Suitable cationic direct dyes include Basic Blue 7, Basic Blue 26, HC Blue 16, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51 Basic Red 76.

As non-ionic direct dyes, non-ionic nitro and quinone dyes and neutral azo dyes can be used. Suitable non-ionic direct dyes are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol.

Anionic direct dyes are also called acid dyes. Acid dyes are direct dyes that have at least one carboxylic acid group (—COOH) and/or one sulphonic acid group (—SO$_3$H). Depending on the pH value, the protonated forms (—COOH, —SO$_3$H) of the carboxylic acid or sulphonic acid groups are in equilibrium with their deprotonated forms (—COO$^-$, —SO$_3$— present). The proportion of protonated forms increases with decreasing pH. If direct dyes are used in the form of their salts, the carboxylic acid groups or sulphonic acid groups are present in deprotonated form and are neutralized with corresponding stoichiometric equivalents of cations to maintain electro neutrality. Inventive acid dyes can also be used in the form of their sodium salts and/or their potassium salts.

The acid dyes within the meaning of the present disclosure have a solubility in water (760 mmHg) at 25° C. of more than 0.5 g/L and are therefore not to be regarded as pigments. Preferably the acid dyes within the meaning of the present disclosure have a solubility in water (760 mmHg) at 25° C. of more than 1.0 g/L.

The alkaline earth salts (such as calcium salts and magnesium salts) or aluminum salts of acid dyes often have a lower solubility than the corresponding alkali salts. If the solubility of these salts is below 0.5 g/L (25° C., 760 mmHg), they do not fall under the definition of a direct dye.

An essential characteristic of acid dyes is their ability to form anionic charges, whereby the carboxylic acid or sulphonic acid groups responsible for this are usually linked to different chromophoric systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

In another embodiment, a process for dyeing keratinous material is exemplified in that the composition (a) comprises at least one anionic direct dye selected from the group including nitrophenylenediamines, nitroaminophenols, azo dyes, anthraquinone dyes, triarylmethane dyes, xanthene dyes, rhodamine dyes, oxazine dyes and/or indophenol dyes, the rhodamine dyes, the oxazine dyes and/or the indophenol dyes, the dyes from the abovementioned group each having at least one carboxylic acid group (—COOH), a sodium carboxylate group (—COONa), a potassium carboxylate group (—COOK), a sulfonic acid group (—SO$_3$H), a sodium sulfonate group (—SO$_3$Na) and/or a potassium sulfonate group (—SO$_3$K).

Suitable acid dyes may include, for example, one or more compounds selected from the following group: Acid Yellow 1 (D&C Yellow 7, Citronin A, Ext. D&C Yellow No. 7, Japan Yellow 403, CI 10316, COLIPA no B001), Acid Yellow 3 (COLIPA no: C 54, D&C Yellow No 10, Quinoline Yellow, E104, Food Yellow 13), Acid Yellow 9 (CI 13015), Acid Yellow 17 (CI 18965), Acid Yellow 23 (COLIPA no C. 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA no C015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodium-salt; Brown No. 201; RESORCIN BROWN; ACID ORANGE 24; Japan Brown 201; D & C Brown No. 1), Acid Red 14 (C.I. 14720), Acid Red 18 (E124, Red 18; CI 16255), Acid Red 27 (E 123, CI 16185, C-Rot 46, Real red D, FD&C Red Nr. 2, Food Red 9, Naphthol red S), Acid Red 33 (Red 33, Fuchsia Red, D&C Red 33, CI 17200), Acid Red 35 (CI C.I. 18065), Acid Red 51 (CI 45430, Pyrosin B, Tetraiod-fluorescein, Eosin J, Iodeosin), Acid Red 52 (CI 45100, Food Red 106, Solar Rhodamine B, Acid Rhodamine B, Red no 106 Pontacyl Brilliant Pink), Acid Red 73 (CI 27290), Acid Red 87 (Eosin, CI 45380), Acid Red 92 (COLIPA no C53, CI 45410), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet no 2, C.I. 60730, COLIPA no C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent Blue AE, Amido blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I. 42100), Acid Green 22 (C.I. 42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black no 401, Naphthalene Black 10B, Amido Black 10B, CI 20 470, COLIPA no B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

For example, the water solubility of anionic direct dyes can be determined in the following way. 0.1 g of the anionic direct dye is placed in a beaker. A stir-fish is added. Then add 100 ml of water. This mixture is heated to 25° C. on a magnetic stirrer while stirring. It is stirred for 60 minutes. The aqueous mixture is then visually assessed. If there are still undissolved residues, the amount of water is increased—for example in steps of 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml water at 25° C., the solubility of the dye is 1.0 g/L.

Acid Yellow 1 is called 8-hydroxy-5,7-dinitro-2-naphthalenesulfonic acid disodium salt and has a solubility in water of at least 40 g/L (25° C.).

Acid Yellow 3 is a mixture of the sodium salts of mono- and sisulfonic acids of 2-(2-quinolyl)-1H-indene-1,3(2H)-dione and has a water solubility of 20 g/L (25° C.).

Acid Yellow 9 is the disodium salt of 8-hydroxy-5,7-dinitro-2-naphthalenesulfonic acid, its solubility in water is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is highly soluble in water at 25° C.

Acid Orange 7 is the sodium salt of 4-[(2-hydroxy-1-naphthyl)azo]benzene sulphonate. Its water solubility is more than 7 g/L (25° C.).

Acid Red 18 is the trinatrium salt of 7-hydroxy-8-[(E)-(4-sulfonato-1-naphthyl)-diazenyl)]-1,3-naphthalene disulfonate and has a very high water solubility of more than 20% by weight.

Acid Red 33 is the diantrium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl)ben-zoic acid, whose solubility in water is indicated as greater than 10 g/L (25° C.).

Acid Blue 9 is the disodium salt of 2-({4-[N-ethyl(3-sulfonatobenzyl]amino]phenyl} {4-[(N-ethyl(3-sulfonato-benzyl)imino]-2,5-cyclohexadien-1-ylidene}methyl)-ben-zenesulfonate and has a solubility in water of more than 20% by weight (25° C.).

In a further embodiment, an agent as contemplated herein is therefore exemplified in that it comprises at least one direct dye (a2) selected from the group including acid yellow 1, acid yellow 3, acid yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The direct-acting dye or dyes can be used in various amounts in the medium, depending on the desired color intensity. Good results were obtained when the agent contains—based on the total weight of the agent—one or more direct dyes (a2) in a total amount of from 0.01 to 10.0% by weight, preferably from 0.1 to 8.0% by weight, more preferably from 0.2 to 6.0% by weight and most preferably from 0.5 to 4.5% by weight.

Furthermore, the composition may also contain at least one photochromic or thermochromic dye as the coloring compound (a2).

Photochromic dyes are dyes that react to irradiation with UV light (sunlight or black light) with a reversible change in hue. In this process, the UV light changes the chemical structure of the dyes and thus their absorption behavior (photochromism).

Thermochromic dyes are dyes that react to temperature changes with a reversible change in hue. In this process, the change in temperature alters the chemical structure of the dyes and thus their absorption behavior (Thermochromism).

The agent may contain—based on the total weight of the composition—one or more photochromic dyes (a2) in a total amount of from 0.01 to 10.0% by weight, preferably from 0.1 to 8.0% by weight, more preferably from 0.2 to 6.0% by weight and most preferably from 0.5 to 4.5% by weight Preservative (a3)

As a third essential ingredient, the compositions as contemplated herein contain at least one preservative (a3). Surprisingly, it has been found that the substances normally used for preservation lead to dyeing results with increased color intensity.

The term preservative is a collective term for substances added to cosmetic formulations to extend their shelf life against the action of microorganisms, insects and other small organisms.

A preservative (a3) in the sense of the present disclosure is a substance whose use in the composition as contemplated herein causes it to pass the preservative loading test according to Ph. Eur. (European Pharmacopoeia), 6th edition, 5.3.1. The preservative load test is performed as follows.

30 g of the composition as contemplated herein to be tested are inoculated with $10^5$ colony forming units (CFU) per 1 g of composition of each of the following test microorganisms: *Pseudomonas aeruginosa* (bacterium), *Staphylococcus aureus* (bacterium), *Candida albicans* (fungus), *Aspergillus brasiliensis* (fungus). After addition of the respective microorganism, the sample is homogenized by stirring using a glass rod and then stored at 20 to 25° C. in the dark. After storage of the inoculated compositions for 7, 14, 21 or 28 days, 1 g of each sample was taken and the CFU contained therein determined. The aim of preservation is to reduce the CFU to a value below the detection limit (for each type of added microorganisms). The preservative test is considered passed if the CFU is below the detection limit after 28 days at the latest.

A particularly strong increase in color intensity was observed when the preservative (a3) was selected from the group including benzyl alcohol, 2-phenoxyethanol, 1-phenoxy-propan-2-ol, isopropanol, ethanol, zinc pyrithione, 4-hydroxybenzoic acid methyl ester, 4-hydroxybenzoic acid propyl ester, benzoic acid, salicylic acid, sorbic acid, formic acid, propionic acid, 2-hydroxydiphenyl, 4-hydroxybenzoic acid, dehydroacetic acid, dibromhexamidine, 10-undecylenic acid, hexetidinum, trichlorocarban, triclosanum, 4-chloro-3,4-dimethylphenol, imidazolidinyl urea, hexamethylenetetramine, 1-(4-chlorophenoxy)-1-(imidazol-1-yl)-3,3-dimethyl-2-butanone, 1,3-bis(hydroxymethyl)-5,5-dimethyl-2,4-imidazolidinedione, 1-hydroxy-4-methyl-6-(2,4,4-trimethylpentyl)-2-pyridone, bromochlorophene, 3-methyl-4-(1-methylethyl)phenol, 5-chloro-2-methyl-3 (2H)-isothiazolone, 2-benzyl-4-chlorophenol, 2-chloroacetamide, chlorhexidine, 4,4-dimethyl-1,3-oxazolidine, 1-phenoxy-propan-2-ol, hexamidinum, 5-ethyl-1-aza-3,7-dioxabicyclo-[3.3.0]-octane, chlorphenesin, sodium hydroxymethyl aminoacetate, benzyl hemiformal, 3-iodo-2-propynyl butylcarbamate, methylisothiazolinone and ethyl lauroyl arginate.

In the context of a further embodiment, a very particularly preferred composition comprises at least one preservative (a3) from the group including benzyl alcohol, 2-phenoxy ethanol, 1-phenoxy-propan-2-ol, isopropanol, ethanol, Zinc pyrithione, 4-hydroxybenzoic acid methyl ester, 4-hydroxybenzoic acid propyl ester, benzoic acid, salicylic acid, sorbic acid, formic acid, propionic acid, 2-hydroxydiphenyl, 4-hydroxybenzoic acid, dehydroacetic acid, dibromhexamidine, 10-undecylenic acid, hexetidinum, trichlorocarban, triclosanum, 4-chloro-3,4-dimethylphenol, imidazolidinyl urea, hexamethylenetetramine, 1-(4-chlorophenoxy)-1-(imidazol-1-yl)-3,3-dimethyl-2-butanone, 1,3-bis(hydroxymethyl)-5,5-dimethyl-2,4-imidazolidinedione, 1-hydroxy-4-methyl-6-(2,4,4-trimethylpentyl)-2-pyridone, bromochlorophene, 3-methyl-4-(1-methylethyl)phenol, 5-chloro-2-methyl-3 (2H)-isothiazolone, 2-benzyl-4-chlorophenol, 2-chloroacetamide, chlorhexidine, 4,4-dimethyl-1, 3-oxazolidine, 1-phenoxy-propan-2-ol, hexamidinum, 5-ethyl-1-aza-3,7-dioxabicyclo-[3.3.0]-octane, chlorphenesin, sodium hydroxymethyl aminoacetate, benzyl hemiformal, 3-iodo-2-propynyl butylcarbamate, methylisothiazolinone and ethyl lauroyl arginate.

Benzyl alcohol is also known as phenylmethanol and has the CAS number 100-51-6.

2-Phenoxyethanol is an ether of phenol with ethylene glycol with the molecular formula $C_8H_{10}O_2$. 2-Phenoxyethanol has the CAS number 122-99-6.

Alternative names for 1-phenoxy-propan-2-ol are 1-phenoxy-2-propanol and phenoxyisopropanol.

1-Phenoxy-propan-2-ol carries the CAS number 770-35-4.

Isopropanol is also known as 2-propanol and has the CAS number 67-63-0.

Ethanol has the CAS number 64-17-5.

Zinc pyrithione is alternatively known as zinc bis[2-pyridinethiolate]-N,N'-dioxide, as 2-pyridinethiol 1-oxide, zinc salt or as zinc 2-mercaptopyridine N-oxide. The CAS number of zinc pyrithione is 13463-41-7.

4-Hydroxybenzoic acid methyl ester or also para-hydroxybenzoic acid methyl ester (is the methyl ester of the aromatic carboxylic acid4-hydroxybenzoic acid and belongs to the parabens. 4-Hydroxybenzoic acid methyl ester has the CAS number 99-76-3.

4-Hydroxybenzoic acid propyl ester or para-hydroxybenzoic acid propyl ester the propyl ester of the aromatic carboxylic acid 4-hydroxybenzoic acid and belongs to the parabens. 4-Hydroxybenzoic acid propyl ester carries the CAS number 94-13-3.

Benzoic acid carries the CAS number 65-85-0.

Salicylic acid is also known alternatively as 2-hydroxybenzoic acid and has the CAS number 69-72-7.

Sorbic acid bears the alternative name 2,4-hexadienoic acid ((2E,4E)-hexa-2,4-dienoic acid) and has the CAS number 110-44-1. The salts of sorbic acid, in particular the sodium salt and the potassium salt, are also included in the invention.

Formic acid is also known as methanoic acid and has the CAS number 64-18-6.

Propionic acid is also known alternatively as propanoic acid and has the CAS number 79-09-4.

2-Hydroxydiphenyl is alternatively known as biphenyl-2-ol or 2-hydroxybiphenyl or orthophenylphenol. 2-Hydroxydiphenyl carries the CAS number 90-43-7.

4-Hydroxybenzoic acid is alternatively known as p-salicylic acid, p-hydroxybenzoic acid and has the CAS number 99-96-7.

Dehydroacetic acid has the alternative name 3-acetyl-6-methyl-2,4(3H)-pyrandione, has the CAS number 520-45-6, and has the structure (K1). The tautomeric forms of dehydroacetic acid are also encompassed by the invention.

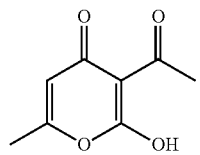

(K1)

Dibromohexamidine is alternatively known as 1,6-bis(4-amidino-2-bromophenoxy)-n-hexane or as, 4'-(hexane-1,6-diyl)-bis-(3-bromobenzamidine) and has CAS number 93856-82-7. Dibromohexamidine has the structure (K2).

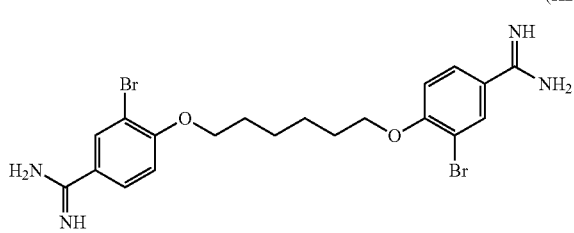

(K2)

10-Undecylenic acid bears the alternative names Undec-10-enoic acid or 10-Undecenoic acid and has the CAS number 112-38-9. 10-Undecylenic acid has the structure of formula (K3). The salts of 10-undecylenic acid, in particular the sodium salt and the potassium salt, are also included in the invention.

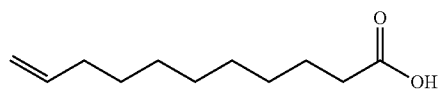

(K3)

Hexetidinum is alternatively known as hexetidine or 1,3-bis(2-ethylhexyl)-5-methylhexahydropyrimidin-5-amine. Hexetidinum or hexetidine has the CAS number 141-94-6. Hexetidinum or hexetidine has the structure of formula (K4).

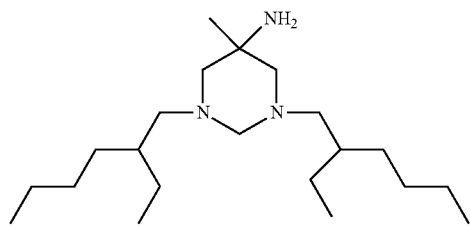

(K4)

Triclocarban also bears the alternative names 3,4,4'-trichlorocarbanilide or 3-(4-chlorophenyl)-1-(3,4-dichlorophenyl)urea and has CAS number 101-20-2. Triclocarban has the structure of formula (K5).

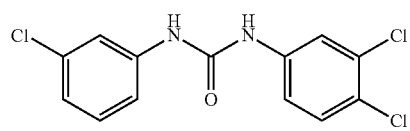

(K5)

Triclosanum or triclosan is alternatively known as 5-chloro-2-(2,4-dichlorophenoxy)-phenol. Triclosanum or trichlosan carries the CAS number 3380-34-5. Triclosanum or triclosan has the structure of formula (K6).

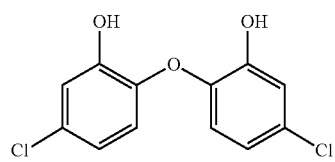

(K6)

4-Chloro-3,4-dimethylphenol is also known as chloroxylenol and has the CAS number 88-04-0.

Imidazolidinyl urea is alternatively referred to as N,N'-methylenebis[N'-(3-hydroxymethyl-2,5-dioxo-4-imidazolidinyl)urea]. Imidazolidinyl urea has the CAS number 39236-46-9 and has the structure of formula (K7).

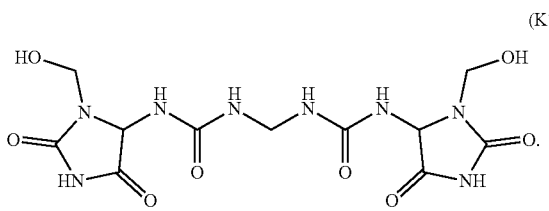

(K7)

Hexamethylenetetramine is also known as urotropine or 1,3,5,7-tetraazaadamantane. Hexamethylenetetramine has the CAS number 100-97-0.

1-(4-Chlorophenoxy)-1-(imidazol-1-yl)-3,3-dimethyl-2-butanone is alternatively known as Climbazole, has CAS number 38083-17-9 and a structure of formula (K8). Structure K8 comprises two enantiomeric forms. Both enantiomers and the mixture of both enantiomers are included in the invention.

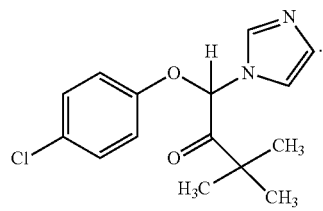

(K8)

1,3-Bis-(hydroxymethyl)-5,5-dimethyl-2,4-imidazolidinedione is also known as DMDM hydantoin, has CAS number 6440-58-0 and has the structure of formula (K9).

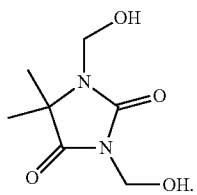

1-Hydroxy-4-methyl-6-(2,4,4-trimethylpentyl)-2-pyridone has the alternative names 1-hydroxy-4-methyl-6-(2,4,4-trimethylpentyl)pyridin-2(1H)-one, octopirox and pirocton olamine and has the CAS number 68890-66-4. Particularly preferably, this preservative is used in the form of its 1:1 adduct with 2-aminoethanol. 1-Hydroxy-4-methyl-6-(2,4,4-trimethylpentyl)-2-pyridone (in the form of its ethanolamine adduct) has the structure of formula (K10).

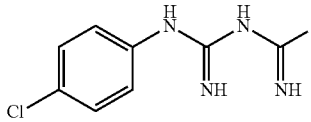

Bromochlorophene has the alternative name 2,2'-methylenebis-(6-bromo-4-chlorophenol) and has the CAS number 15435-29-7. Bromochlorophene has the structure of formula (K11).

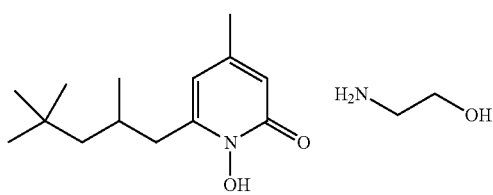

3-Methyl-4-(1-methylethyl)phenol has the alternative names o-cymen-5-ol, p-thymol, biosol and 1-hydroxy-3-methyl-4-isopropylbenzene and has the CAS number 3228-02-2.

5-Chloro-2-methyl-3(2H)-isothiazolone is alternatively known as 5-chloro-2-methyl-4-isothiazolin-3-one or chloromethylisothiazolone, has the CAS number 26172-55-4 and has the structure of formula (K12).

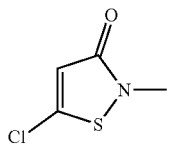

2-Benzyl-4-chlorophenol is alternatively known as chlorophenum or chlorophene and has the CAS number 120-32-1.

2-Chloroacetamide bears the alternative name chloroacetic acid amide and has the CAS number 79-07-2.

Chlorhexidine is alternatively known as 1,1'-hexamethylene bis[5-(4-chlorophenyl)biguanide] and has CAS number 55-56-1. Chlorhexidine has the structure of formula (K13).

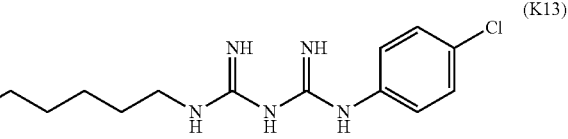

4,4-Dimethyl-1,3-oxazolidine has the CAS number 51200-87-4.

1-Phenoxy-propan-2-ol is alternatively known as phenyl-O-hydroxypropyl ether, 1-phenoxy-2-propanol, phenoxyisopropanol, propylene phenoxetol, 2-phenoxy-1-methylethanol or propylene glycol 1-phenyl ether and has CAS number 770-35-4.

Hexamidinum is alternatively known as hexamidine or 1,6-bis(4-amidinophenoxy)-n-hexane or 4,4'-[hexane-1,6-diylbis(oxy)]dibenzenecarboximidamide and has the CAS no. 3811-75-4.

Hexamidine has the structure of formula (K14).

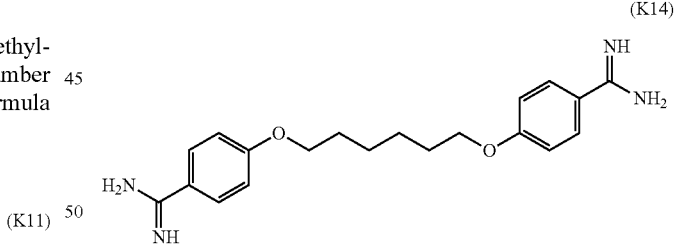

5-Ethyl-1-aza-3,7-dioxabicyclo-[3.3.0]-octane is alternatively also known as 5-ethyl-3,7-dioxa-1-azabicyclo-[3.3.0]octane or dihydro-7a-ethyloxazolo[3,4-c]oxazole, has the CAS number 7747-35-5 and has the structure of formula (K15)

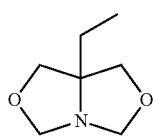

Chlorphenesin is also known alternatively as (3-(4-chlorophenoxy)-2-hydroxypropyl)carbamate and has the CAS number 886-74-8. Chlorphenesin has the structure of formula (K16).

(K16)

Sodium hydroxymethyl aminoacetate is alternatively known as sodium N-(hydroxymethyl)glycinate or sodium N-(hydroxymethyl)glycinate, has the CAS number 70161-44-3, and has the structure of the formula (K17)

(K17)

Benzylhemiformal is also known alternatively as (benzyloxy)methanol and has the CAS number 14548-60-8).

3-Iodo-2-propynyl butylcarbamate is alternatively known as 3-iodopropargyl-N-butylcarbamate or biodocarb and has the CAS number 55406-53-6. 3-Iodo-2-propynyl butylcarbamate has the structure of formula (K18).

(K18)

Methylisothiazolinone is alternatively known as 2-methyl-2H-isothiazol-3-one and has the CAS number 2682-20-4.

Ethyl lauroyl arginate is also known alternatively as ethyl Na-dodecanoyl-L-arginate hydrochloride or Monohydrochloride of L-arginine or Na-lauroyl-ethyl ester and has the CAS number 60372-77-2. Ethyl lauroyl arginate has the structure of formula (K19) and can be used either as a free compound or in the form of its hydrochloride salt.

(K19)

Preservatives (a3) are also used with preference in certain ranges of amounts in the composition as contemplated herein.

Particularly good results were obtained when the composition contained—based on the total weight of the composition—one or more preservatives (a3) in a total amount of from 0.01 to 5.0% by weight, preferably from 0.1 to 2.5% by weight, more preferably from 0.15 to 1.0% by weight and most preferably from 0.2 to 0.8% by weight.

In a further preferred embodiment, a composition as contemplated herein contains—based on the total weight of the composition—one or more preservatives (a3) in a total amount of from 0.01 to 5.0% by weight, preferably from 0.1 to 2.5% by weight, more preferably from 0.15 to 1.0% by weight and very particularly preferably from 0.2 to 0.8% by weight.

The very best results were obtained when benzyl alcohol was used as the preservative (a3), since a particularly strong enhancement of color intensity was observed with benzyl alcohol.

In the context of a further very particularly preferred embodiment, a composition as contemplated herein contains benzyl alcohol (a3).

Benzyl alcohol is also preferably used in certain ranges of amounts in the composition as contemplated herein. It has been found to be particularly advantageous if the composition contains—based on the total weight of the composition—0.1 to 1.5% by weight, preferably 0.2 to 1.0% by weight, more preferably 0.3 to 0.9% and most preferably 0.4 to 0.8% by weight of benzyl alcohol.

In a further explicitly very particularly preferred embodiment, a composition as contemplated herein contains—based on the total weight of the composition—0.1 to 1.5% by weight, preferably 0.2 to 1.0% by weight, further preferably 0.3 to 0.9% and very particularly preferably 0.4 to 0.8% by weight of benzyl alcohol.

Fat Components (a4)

As a fourth constituent essential to the invention, the composition as contemplated herein contains at least one fat constituent (a4). It has been found that the use of at least one fatty ingredient (a4) results in the agent being in the form of an emulsion, which has the optimum viscosity and has also been found to be beneficial in terms of improving color intensity.

The fatty components are hydrophobic substances that can form emulsions in the presence of water, forming micelle systems. Without being committed to this theory, it is assumed that the $C_1$-$C_6$ alkoxysilanes—either in the form of their monomers or possibly in the form of their condensed oligomers—are embedded in this hydrophobic environment or in the micelle systems so that the polarity of their environment changes. Due to the hydrophobic character of the fatty components, the environment of the $C_1$-$C_6$ alkoxysilanes is also hydrophobised. It is assumed that the polymerization reaction of the $C_1$-$C_6$ alkoxy silanes leading to the film or coating takes place in an environment of reduced polarity at reduced speed.

For the purposes of the invention, "fatty components" means organic compounds with a solubility in water at room temperature (22° C.) and atmospheric pressure (760 mmHg) of less than 1% by weight, preferably less than 0.1% by weight. The definition of fat constituents explicitly covers only uncharged (i.e., non-ionic) compounds. Fat components have at least one saturated or unsaturated alkyl group with at least 12 C atoms. The molecular weight of the fat constituents is a maximum of 5000 g/mol, preferably a maximum of 2500 g/mol and particularly preferably a maximum of 1000 g/mol. The fat components are neither polyoxyalkylated nor polyglycerylated compounds.

Very preferably, the fat constituents (a4) contained in the composition are selected from the group including $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons.

In the context of a further preferred embodiment, an agent as contemplated herein contains one or more fat constituents (a4) from the group including the $C_{12}$-$C_{30}$ fatty alcohols, the $C_{12}$-$C_{30}$ fatty acid triglycerides, the $C_{12}$-$C_{30}$ fatty acid monoglycerides, the $C_{12}$-$C_{30}$ fatty acid diglycerides and/or the hydrocarbons.

In this context, very particularly preferred fat constituents are understood to be constituents from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons. For the purposes of the present disclosure, only non-ionic substances are explicitly regarded as fat components. Charged compounds such as fatty acids and their salts are not considered to be fat components.

The $C_{12}$-$C_{30}$ fatty alcohols can be saturated, mono- or polyunsaturated, linear or branched fatty alcohols with 12 to 30 C atoms.

Examples of preferred linear, saturated $C_{12}$-$C_{30}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, Cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Preferred linear unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidone alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol).

The preferred representatives for branched fatty alcohols are 2-octyl-dodecanol, 2-hexyl-dodecanol and/or 2-butyl-dodecanol.

In a further preferred embodiment, an agent as contemplated herein comprises one or more $C_{12}$-$C_{30}$ fatty alcohols (a4) selected from the group including Dodecan-1-ol (dodecyl alcohol, lauryl alcohol),
Tetradecan-1-ol (tetradecyl alcohol, myristyl alcohol),
Hexadecan-1-ol (hexadecyl alcohol, cetyl alcohol, palmityl alcohol),
Octadecan-1-ol (octadecyl alcohol, stearyl alcohol),
Arachyl alcohol (eicosan-1-ol),
Heneicosyl alcohol (heneicosan-1-ol),
Behenyl alcohol (docosan-1-ol),
(9Z)-Octadec-9-en-1-ol (oleyl alcohol),
(9E)-Octadec-9-en-1-ol (elaidyl alcohol),
(9Z,12Z)-Octadeca-9,12-dien-1-ol (linoleyl alcohol),
(9Z,12Z,15Z)-Octadeca-9,12,15-trien-1-ol (linolenoyl alcohol),
Gadoleyl alcohol ((9Z)-Eicos-9-en-1-ol),
Arachidonic alcohol ((5Z,8Z,11Z,14Z)-Eicosa-5,8,11,14-tetraen-1-ol),
Erucyl alcohol ((13Z)-docos-13-en-1-ol),
Brassidyl alcohol ((13E)-docosen-1-ol),
2-Octyl-dodecanol,
2-hexyl dodecanol and/or
2-Butyl-dodecanol contains.

It has been found to be particularly preferable to use one or more $C_{12}$-$C_{30}$ fatty alcohols (a4) in very specific ranges of amounts.

It is particularly preferred if the composition contains one or more $C_{12}$-$C_{30}$ fatty alcohols in a total amount of from 2.0 to 50.0% by weight, preferably from 3.0 to 30.0% by weight, more preferably from 4.0 to 20.0% by weight, still more preferably from 5.0 to 15.0% by weight and most preferably from 5.0 to 10.0% by weight, based on the total weight of the composition.

Further, as a wholly suitable fat ingredient, the composition (a4) may also contain at least one $C_{12}$-$C_{30}$ fatty acid triglyceride that is $C_{12}$-$C_{30}$ fatty acid monoglyceride and/or $C_{12}$-$C_{30}$ fatty acid diglyceride. For the purposes of the present disclosure, a $C_{12}$-$C_{30}$ fatty acid triglyceride is understood to be the triester of the trivalent alcohol glycerol with three equivalents of fatty acid. Both structurally identical and different fatty acids within a triglyceride molecule can be involved in the formation of esters.

As contemplated herein, fatty acids are to be understood as saturated or unsaturated, unbranched or branched, unsubstituted or substituted $C_{12}$-$C_{30}$ carboxylic acids. Unsaturated fatty acids can be mono- or polyunsaturated. For an unsaturated fatty acid, its C—C double bond(s) may have the Cis or Trans configuration.

Fatty acid triglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid, linolenic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], and/or nervonic acid [(15Z)-tetracos-15-enoic acid].

The fatty acid triglycerides can also be of natural origin. The fatty acid triglycerides or mixtures thereof occurring in soybean oil, peanut oil, olive oil, sunflower oil, macadamia nut oil, moringa oil, apricot kernel oil, marula oil and/or optionally hardened castor oil are particularly suitable for use in the product as contemplated herein.

A $C_{12}$-$C_{30}$ fatty acid monoglyceride is understood to be the monoester of the trivalent alcohol glycerol with one equivalent of fatty acid. Either the middle hydroxy group of glycerol or the terminal hydroxy group of glycerol may be esterified with the fatty acid.

$C_{12}$-$C_{30}$ fatty acid monoglycerides are particularly suitable in which a hydroxyl group of glycerol is esterified with a fatty acid, the fatty acids being selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid, linolenic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], or nervonic acid [(15Z)-tetracos-15-enoic acid].

A $C_{12}$-$C_{30}$ fatty acid diglyceride is the diester of the trivalent alcohol glycerol with two equivalents of fatty acid. Either the middle and one terminal hydroxy group of glycerol may be esterified with two equivalents of fatty acid, or both terminal hydroxy groups of glycerol are esterified with one fatty acid each. The glycerol can be esterified with two structurally identical fatty acids or with two different fatty acids.

Fatty acid triglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid, linolenic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], and/or nervonic acid [(15Z)-tetracos-15-enoic acid].

Particularly good results were obtained when composition (B) contained at least one $C_{12}$-$C_{30}$ fatty acid monoglyceride selected from the monoesters of glycerol with one equivalent of fatty acid selected from the group including dodecanoic acid (lauric acid), Tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), Petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid, linolenic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid] and/or nervonic acid [(15Z)-tetracos-15-enoic acid].

In the context of a further embodiment, a composition as contemplated herein comprises at least one $C_{12}$-$C_{30}$ fatty acid monoglyceride selected from the monoesters of glycerol with one equivalent of fatty acid from the group including dodecanoic acid, tetradecanoic acid, hexadecanoic acid, tetracosanoic acid, octadecanoic acid, eicosanoic acid and/or docosanoic acid.

It has been shown to be preferable to use one or more $C_{12}$-$C_{30}$ fatty acid mono-, $C_{12}$-$C_{30}$ fatty acid di- and/or $C_{12}$-$C_{30}$ fatty acid triglycerides (a4) in very specific ranges of amounts in the composition.

Regarding the solution of the problem as contemplated herein, it has proved advantageous if the composition—based on the total weight of the composition—contained one or more $C_{12}$-$C_{30}$ fatty acid mono-, $C_{12}$-$C_{30}$ fatty acid di- and/or $C_{12}$-$C_{30}$ fatty acid triglycerides (a4) in a total amount of 0.1 to 20.0 wt.-%, preferably from 0.3 to 15.0% by weight, more preferably from 0.5 to 10.0% by weight and most preferably from 0.8 to 5.0% by weight.

In a very particularly preferred embodiment, a process as contemplated herein is exemplified in that the composition contains—based on the total weight of the composition—one or more $C_{12}$-$C_{30}$ fatty acid mono-, $C_{12}$-$C_{30}$ fatty acid di- and/or $C_{12}$-$C_{30}$ fatty acid triglycerides in a total amount of from 0.1 to 20.0% by weight, preferably from 0.3 to 15.0% by weight, more preferably from 0.5 to 10.0% by weight and very particularly preferably from 0.8 to 5.0% by weight.

The $C_{12}$-$C_{30}$ fatty acid mono-, $C_{12}$-$C_{30}$ fatty acid di- and/or $C_{12}$-$C_{30}$ fatty acid triglycerides may be used as the sole fat components (a4) in the compositions. However, it may also be suitable as contemplated herein to incorporate at least one $C_{12}$-$C_{30}$ fatty acid mono-, $C_{12}$-$C_{30}$ fatty acid di- and/or $C_{12}$-$C_{30}$ fatty acid triglyceride in combination with at least one $C_{12}$-$C_{30}$ fatty alcohol into the composition.

Furthermore, as a very particularly preferred fatty constituent (a4), the composition may also contain at least one hydrocarbon.

Hydrocarbons are compounds consisting exclusively of the atoms carbon and hydrogen with 8 to 80 C atoms. In this context, aliphatic hydrocarbons such as mineral oils, liquid paraffin oils (e.g., Paraffinum Liquidum or Paraffinum Perliquidum), isoparaffin oils, semi-solid paraffin oils, paraffin waxes, hard paraffin (Paraffinum Solidum), Vaseline and polydecenes are particularly preferred.

Liquid paraffin oils (Paraffinum Liquidum and Paraffinum Perliquidum) have proven to be particularly suitable in this context. Paraffinum Liquidum, also known as white oil, is the preferred hydrocarbon. Paraffinum Liquidum is a mixture of purified, saturated, aliphatic hydrocarbons, consisting mainly of hydrocarbon chains with a C-chain distribution of 25 to 35 C-atoms.

Very particularly good results were obtained when the composition contained at least one hydrocarbon (a4) selected from the group including mineral oils, liquid kerosene oils, isoparaffin oils, semisolid kerosene oils, kerosene waxes, hard kerosene (Paraffinum solidum), petrolatum and polydecenes.

In a very particularly preferred embodiment, a composition as contemplated herein comprises at least one fatty constituent (a4) from the group of hydrocarbons.

Regarding the solution of the problem as contemplated herein, it proved to be quite particularly preferable if the composition contained—based on the total weight of the composition—one or more hydrocarbons (a4) in a total amount of from 0.5 to 20.0% by weight, preferably from 0.7 to 10.0% by weight, more preferably from 0.9 to 5.0% by weight and most preferably from 1.0 to 4.0% by weight.

In a very particularly preferred embodiment, an agent as contemplated herein contains—based on the total weight of the agent—one or more hydrocarbons (a4) in a total amount of in a total amount of from 0.5 to 20.0% by weight, preferably from 0.7 to 10.0% by weight, more preferably from 0.9 to 5.0% by weight and very particularly preferably from 1.0 to 4.0% by weight.

The hydrocarbon(s) may be used as the sole fatty ingredients (a4) in the compositions. However, it is also as contemplated herein to incorporate at least one hydrocarbon in combination with at least one other constituent into the compositions.

Very preferably, the composition contains at least one fatty constituent (a4) from the group of $C_{12}$-$C_{30}$ fatty alcohols and at least one further fatty constituent from the group of hydrocarbons.

Average Water Content

The agent described above is a ready-to-use agent that can be applied to the keratinous material. This ready-to-use agent preferably has a high water content. It has been found that particularly suitable agents are those containing—based on the total weight of the agent—50.0 to 98.0% by weight, preferably 60.0 to 90.0% by weight, more preferably 70.0 to 90.0% by weight and most preferably 75.0 to 90.0% by weight of water.

In a further explicitly quite particularly preferred embodiment, an agent as contemplated herein contains—based on the total weight of the agent—50.0 to 98.0% by weight, preferably 60.0 to 90.0% by weight, further preferably 70.0 to 90.0% by weight and very particularly preferably 75.0 to 90.0% by weight of water.

Surfactants in the Medium

Due to its content of water and fat constituent (a4), the agent as contemplated herein is particularly preferably in the form of an emulsion. To further optimize the formation of the emulsion, it has proven particularly preferable to continue to use at least one surfactant in the agent.

Very preferably, therefore, the composition additionally contains at least one surfactant.

In the context of a further particularly preferred embodiment, an agent as contemplated herein comprises at least one surfactant, The term surfactants (T) refer to surface-active substances that can form adsorption layers on surfaces and interfaces or aggregate in bulk phases to form micelle colloids or lyotropic mesophases. A distinction is made between anionic surfactants including a hydrophobic residue and a negatively charged hydrophilic head group, amphoteric surfactants, which carry both a negative and a compensating positive charge, cationic surfactants, which in addition to a hydrophobic residue have a positively charged hydrophilic group, and non-ionic surfactants, which have no charges but strong dipole moments and are strongly hydrated in aqueous solution.

In a very particularly preferred embodiment, an agent as contemplated herein comprises at least one nonionic surfactant.

Non-ionic surfactants contain, for example, a polyol group, a polyalkylene glycol ether group or a combination of polyol and polyglycol ether group as the hydrophilic group. Such links include Addition products of 2 to 50 mol ethylene oxide and/or 0 to 5 mol propylene oxide to linear and branched fatty alcohols with 6 to 30 C atoms, the fatty alcohol polyglycol ethers or the fatty alcohol polypropylene glycol ethers or mixed fatty alcohol polyethers, Addition products of 2 to 50 mol ethylene oxide and/or 0 to 5 mol propylene oxide to linear and branched fatty acids with 6 to 30 C atoms, the fatty acid polyglycol ethers or the fatty acid polypropylene glycol ethers or mixed fatty acid polyethers, Addition products of 2 to 50 mol ethylene oxide and/or 0 to 5 mol propylene oxide to linear and branched alkylphenols having 8 to 15 C atoms in the alkyl group, the alkylphenol polyglycol ethers or the alkylpolypropylene glycol ethers or mixed alkylphenol polyethers, with a methyl or $C_2$-$C_6$-alkyl radical end-group capped addition products of 2 to 50 moles of ethylene oxide and/or 0 to 5 moles of propylene oxide to linear and branched fatty alcohols with 8 to 30 C atoms, to fatty acids with 8 to 30 C atoms and to alkylphenols with 8 to 15 C atoms in the alkyl group, such as the grades available under the sales names Dehydol® LS, Dehydol® LT (Cognis), $C_{12}$-$C_{30}$ fatty acid mono- and diesters of addition products of 1 to 30 mol ethylene oxide to glycerol, Addition products of 5 to 60 mol ethylene oxide to castor oil and hardened castor oil, Polyol fatty acid esters, such as the commercial product Hydagen® HSP (Cognis) or Sovermol® grades (Cognis), alkoxylated triglycerides, alkoxylated fatty acid alkyl esters of the formula (Tnio-1)

 (Tnio-1)

in which $R^1CO$ is a linear or branched, saturated and/or unsaturated acyl radical having 6 to 22 carbon atoms, $R^2$ is hydrogen or methyl, $R^3$ is linear or branched alkyl radicals having 1 to 4 carbon atoms and w is numbers from 1 to 20, amine oxides, Hydroxy mixed ethers, as described for example in DE-OS 19738866, Sorbitan fatty acid esters and addition products of ethylene oxide to sorbitan fatty acid esters such as polysorbates, Sugar fatty acid esters and addition products of ethylene oxide to sugar fatty acid ester, Addition products of ethylene oxide to fatty acid alkanolamides and fatty amines, Sugar tensides of the alkyl and alkenyl oligoglycoside type according to formula (E4-II),

 (Tnio-2)

in which $R^4$ is an alkyl or alkenyl radical containing 4 to 22 carbon atoms, G is a sugar residue containing 5 or 6 carbon atoms and p is several 1 to 10. They can be obtained by the relevant methods of preparative organic chemistry. The alkyl and alkenyl oligoglycosides can be derived from aldoses or ketoses with 5 or 6 carbon atoms, preferably glucose. The preferred alkyl and/or alkenyl oligoglycosides are thus alkyl and/or alkenyl oligoglucosides. The index number pin the general formula (Tnio-2) indicates the degree of oligomerization (DP), i.e., the distribution of mono- and oligoglycosides and stands for a number between 1 and 10. While p must always be an integer in the individual molecule and can assume the values p=1 to 6, the value p for a certain alkyl oligoglycoside is an analytically determined arithmetical quantity, which usually represents a fractional number. Preferably alkyl and/or alkenyl oligoglycosides with an average degree of oligomerization p of 1.1 to 3.0 are used. From an application technology point of view, those alkyl and/or alkenyl oligoglycosides are preferred whose degree of oligomerization is less than 1.7 and lies between 1.2 and 1.4. The alkyl or alkenyl radical $R^4$ can be derived from primary alcohols containing 4 to 11, preferably 8 to 10 carbon atoms. Typical examples are butanol, caproic alcohol, caprylic alcohol, caprin alcohol and undecrylic alcohol as well as their technical mixtures, such as those obtained in the hydrogenation of technical fatty acid methyl esters or during the hydrogenation of aldehydes from Roelen's oxo synthesis. Preferred are alkyl oligoglucosides with a chain length of $C_8$-$C_{10}$ (DP=1 to 3), which are obtained as a preliminary step in the distillative separation of technical $C_8$-$C_{18}$ coconut-fatty alcohol and may be contaminated with less than 6% by weight of $C_{12}$ alcohol, and alkyl oligoglucosides based on technical $C_{9/11}$ oxoalcohols (DP=1 to 3). The alkyl or alkenyl radical $R^{15}$ can also be derived from primary alcohols having 12 to 22, preferably 12 to 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and their technical mixtures, which can be obtained as described above. Preferred are alkyl oligoglucosides based on hardened $C_{12/14}$ coconut alcohol with a DP of 1 to 3.

Sugar surfactants of the fatty acid N-alkyl polyhydroxyalkylamide type, a nonionic surfactant of formula (Tnio-3)

 (Tnio-3)

in which $R^5CO$ is an aliphatic acyl radical containing 6 to 22 carbon atoms, $R^6$ is hydrogen, an alkyl or hydroxyalkyl radical containing 1 to 4 carbon atoms and [Z] is a linear or branched polyhydroxyalkyl radical containing 3 to 12 carbon atoms and 3 to 10 hydroxyl groups. The fatty acid N-alkyl polyhydroxyalkylamides are known substances that can usually be obtained by reductive amination of a reducing sugar with ammonia, an alkylamine or an alkanolamine and subsequent acylation with a fatty acid, a fatty acid alkyl ester or a fatty acid chloride. The fatty acid N-alkyl polyhydroxyalkylamides are preferably derived from reducing sugars with 5 or 6 carbon atoms, especially from glucose. The preferred fatty acid N-alkyl polyhydroxyalkylamides are therefore fatty acid N-alkylglucamides as represented by the formula (Tnio-4):

$$R^7CO\text{---}(NR^8)\text{---}CH_2\text{---}[CH(OH)]_4\text{---}CH_2OH \qquad \text{(Tnio-4)}$$

Preferably, glucamides of the formula (Tnio-4) are used as fatty acid-N-alkyl polyhydroxyalkylamides, in which $R^8$ represents hydrogen or an alkyl group and $R^7CO$ represents the acyl radical of caproic acid, caprylic acid, capric acid, Lauric acid, myristic acid, palmitic acid, palmoleic acid, stearic acid, isostearic acid, oleic acid, elaidic acid, petroselinic acid, linoleic acid, linolenic acid, arachidic acid, gadoleic acid, behenic acid or erucic acid or their technical mixtures. Particularly preferred are fatty acid N-alkyl glucamides of the formula (Tnio-4), which are obtained by reductive amination of glucose with methylamine and subsequent acylation with lauric acid or $C_{12/14}$ coconut fatty acid or a corresponding derivative. Furthermore, polyhydroxyalkylamides can also be derived from maltose and palatinose.

The sugar surfactants may preferably be present in the compositions used as contemplated herein in amounts of 0.1-20% by weight, based on the total composition. Amounts of 0.5-15 wt. % are preferred and amounts of 0.5-7.5 wt. % are particularly preferred.

Other typical examples of nonionic surfactants are fatty acid amide polyglycol ethers, fatty amine polyglycol ethers, mixed ethers or mixed formals, protein hydrolysates (especially wheat-based vegetable products) and polysorbates.

The alkylene oxide addition products to saturated linear fatty alcohols and fatty acids, each with 2 to 30 moles of ethylene oxide per mole of fatty alcohol or fatty acid, and the sugar surfactants have proved to be preferred nonionic surfactants. Preparations with excellent properties are also obtained if they contain fatty acid esters of ethoxylated glycerol as non-ionic surfactants.

These connections are identified by the following parameters. The alkyl radical R contains 6 to 22 carbon atoms and can be either linear or branched. Primary linear and in 2-position methyl-branched aliphatic radicals are preferred. Such alkyl radicals are for example 1-octyl, 1-decyl, 1-lauryl, 1-myristyl, 1-cytyl and 1-stearyl. Especially preferred are 1-octyl, 1-decyl, 1-lauryl, 1-myristyl. When so-called "oxo-alcohols" are used as starting materials, compounds with an odd number of carbon atoms in the alkyl chain predominate.

The compounds with alkyl groups used as surfactants can each be uniform substances. However, it is usually preferable to start from native plant or animal raw materials in the production of these substances, so that one obtains substance mixtures with different alkyl chain lengths depending on the respective raw material.

For surfactants which are products of the addition of ethylene and/or propylene oxide to fatty alcohols or derivatives of these addition products, both products with a "normal" homologue distribution and those with a narrowed homologue distribution can be used. By "normal" homologue distribution we mean mixtures of homologues obtained in the reaction of fatty alcohol and alkylene oxide using alkali metals, alkali metal hydroxides or alkali metal alcoholates as catalysts. Constricted homologue distributions are obtained, on the other hand, when, for example, hydrotalcites, alkaline earth metal salts of ether carboxylic acids, alkaline earth metal oxides, hydroxides or alcoholates are used as catalysts. The use of products with narrowed homologue distribution may be preferred.

Particularly good results were obtained when an agent (b) containing at least one ethoxylated fatty alcohol with a degree of ethoxylation of 80 to 120 was used in the process as contemplated herein.

In another very particularly preferred embodiment, an agent as contemplated herein comprises at least one nonionic surfactant of the formula (T-I), $$Ra\text{---}[O\text{---}CH_2\text{---}CH_2]_n\text{---}OH \qquad \text{(T-I)}$$

wherein Ra represents a saturated or unsaturated, straight or branched $C_8$-$C_{24}$ alkyl group, preferably a saturated, straight $C_{16}$-bis $C_{18}$ alkyl group, and n is an integer from 80 to 120, preferably an integer from 90 to 110, and particularly preferably the number 100.

A particularly well-suited nonionic surfactant of this type bears the trade name Brij S 100 or Brij S 100 PA SG. This is stearyl alcohol, ethoxylated with 100 EO, which is commercially available from Croda and has the CAS number 9005-00-9.

Furthermore, particularly good results were obtained when an agent as contemplated herein was used which contained at least one ethoxylated fatty alcohol with a degree of ethoxylation of 10 to 40.

In another very particularly preferred embodiment, an agent as contemplated herein comprises at least one nonionic surfactant of the formula (T-II), $$Rb\text{---}[O\text{---}CH_2\text{---}CH_2]_m\text{---}OH \qquad \text{(T-II)}$$

wherein

Ra is a saturated or unsaturated, unbranched or branched $C_8$-$C_{24}$ alkyl group, preferably a saturated, unbranched $C_{16}$- to $C_{18}$ alkyl group, and m an integer from 10 to 40, preferably an integer from 20 to 35, and particularly preferably the number 30.

A particularly well-suited nonionic surfactant of this type is ceteareth-30. Ceteareth-30 is a mixture of cetyl alcohol and stearyl alcohol, each ethoxylated with 30 units of ethylene oxide. The mixture of cetyl alcohol and stearyl alcohol is called cetearyl alcohol. Ceteareth-30 has the CAS number 68439-49-6 and can be purchased, for example, under the trade name Eumulgin B3 from BASF.

It has been found to be quite preferred if the composition contains both at least one nonionic surfactant of formula (T-I) and at least one nonionic surfactant of formula (T-II).

Other Optional Ingredients in the Agent

In addition to the ingredients (a1) to (a4) essential to the invention already described, the composition may also contain further optional ingredients.

For example, the agent may contain a film-forming polymer. The film-forming polymer may be selected, for example, from the group including polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers, explicitly very particularly preferred polyvinylpyrrolidone (PVP).

Further appropriate film-forming polymers can be selected from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

Film-forming polymers selected from the group of synthetic polymers, polymers obtainable by free-radical polymerization, or natural polymers have proven to be well suited.

Other particularly well-suited film-forming polymers can be selected from the homopolymers or copolymers of oleofins, such as cycloolefins, butadiene, isoprene or styrene, vinyl ethers, vinyl amides, the esters or amides of (meth) acrylic acid having at least one $C_1$-$C_{20}$ alkyl group, an aryl group or a $C_2$-$C_{10}$ hydroxyalkyl group.

Other film-forming polymers may be selected from the homo- or copolymers of isooctyl (meth)acrylate; isononyl (meth)acrylate; 2-ethylhexyl (meth)acrylate; lauryl (meth) acrylate); isopentyl (meth)acrylate; n-butyl (meth)acrylate); isobutyl (meth)acrylate; ethyl (meth)acrylate; methyl (meth) acrylate; tert-butyl (meth)acrylate; stearyl (meth)acrylate; hydroxyethyl (meth)acrylate; 2-hydroxypropyl (meth)acrylate; 3-hydroxypropyl (meth)acrylate; and/or mixtures thereof.

Further film-forming polymers may be selected from the homo- or copolymers of (meth)acrylamide; N-alkyl-(meth) acrylamides, in those with $C_2$-$C_{18}$ alkyl groups, such as N-ethyl-acrylamide, N-tert-butyl-acrylamide, le N-octyl-crylamide; N-di($C_1$-$C_4$)alkyl-(meth)acrylamide.

Other suitable anionic copolymers include copolymers of acrylic acid, methacrylic acid or their $C_1$-$C_6$ alkyl esters, as sold under the INCI declaration Acrylates Copolymers. A suitable commercial product is for example Aculyn® 33 from Rohm & Haas. Copolymers of acrylic acid, methacrylic acid or their $C_1$-$C_6$ alkyl esters and the esters of an ethylenically unsaturated acid and an alkoxylated fatty alcohol are also preferred. Suitable ethylenically unsaturated acids are especially acrylic acid, methacrylic acid and itaconic acid; suitable alkoxylated fatty alcohols are especially steareth-20 or ceteth-20.

Polymers on the market include Aculyn® 22 (Acrylate/Steareth-20 Me-thacrylate Copolymer), Aculyn® 28 (Acrylate/Beheneth-25 Methacrylate Copolymer), Structure 2001® (Acryla-tes/Steareth-20 Itaconate Copolymer), Structure 3001® (Acrylate/Ceteth-20 Itaconate Copolymer), Structure Plus® (acrylate/aminoacrylate C10-30 alkyl PEG-20 itaconate copolymer), Carbopol® 1342, 1382, Ultrez 20, Ultrez 21 (acrylate/C10-30 alkyl acrylate crosspolymer), Synthalen W 2000® (acrylate/palmeth-25 acrylate copolymer) or Soltex OPT (acrylate/$C_{12}$-22 alkyl methacrylate copolymer) distributed by Rohme and Haas.

The homo- and copolymers of N-vinylpyrrolidone, vinyl-caprolactam, vinyl-(C1-C6)alkyl-pyrrole, vinyl-oxazole, vinyl-thiazole, vinylpyrimidine, vinylimidazole can be named as suitable polymers based on vinyl monomers.

Also suitable are the copolymers octylacrylamide/acrylates/butylaminoethyl methacrylate copolymer, such as those sold commercially under the trade names AMPHO-MER® or LOVOCRYL® 47 from NATIONAL STARCH, or the copolymers of acrylates/octylacrylamides sold under the trade names DERMACRYL® LT and DERMACRYL® 79 from NATIONAL STARCH.

Suitable olefin-based polymers include homopolymers and copolymers of ethylene, propylene, butene, isoprene and butadiene.

In another version, block copolymers can be used as film-forming hydrophobic polymers, which comprise at least one block of styrene or the derivatives of styrene. These block copolymers can be copolymers that contain one or more other blocks in addition to a styrene block, such as styrene/ethylene, styrene/ethylene/butylene, styrene/butylene, styrene/isoprene, styrene/butadiene. Such polymers are commercially distributed by BASF under the trade name "Luvitol HSB".

If, in principle, both anionic and cationic and/or nonionic polymers can be used in the composition as contemplated herein, it has proved particularly preferable not to use further ionic compounds or to use them only in small amounts. In other words, a particularly strong improvement in color intensity could be achieved when the agent was a predominantly non-ionic base and therefore contained cationic and anionic polymers either not at all or only in very small amounts. For this reason, it has been found to be particularly preferable if the total content of all anionic polymers contained in the agent is below 0.1% by weight. Furthermore, it has been found to be particularly preferred if the total content of all cationic polymers contained in the agent is below 0.1% by weight. The amount of catalytic or anionic polymer is related to the total weight of the agent.

In another very particularly preferred embodiment, a means as contemplated herein is exemplified in that—in relation to the total weight of the means the total content of all anionic polymers contained in the composition is below 0.1% by weight, and the total content of all cationic polymers contained in the composition is below 0.1% by weight.

In addition to the non-ionic surfactants described above, the agents can in principle also contain one or more charged surfactants. The term surfactants refer to surface-active substances. A distinction is made between anionic surfactants including a hydrophobic residue and a negatively charged hydrophilic head group, amphoteric surfactants, which carry both a negative and a compensating positive charge, cationic surfactants, which in addition to a hydrophobic residue have a positively charged hydrophilic group, and non-ionic surfactants, which have no charges but strong dipole moments and are strongly hydrated in aqueous solution.

Zwitterionic surfactants are those surface-active compounds which carry at least one quaternary ammonium group and at least one —COO$^{(-)}$— or —SO$_3^{(-)}$ group in the molecule. Particularly suitable zwitterionic surfactants are the so-called betaines such as the N-alkyl-N,N-dimethylammonium-glycinate, for example the cocoalkyl-dimethylammoniumglycinate, N-acylaminopropyl-N,N-dimethylammoniumglycinate, for example, cocoacylaminopropyl dimethyl ammonium glycinate, and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI name cocamidopropyl betaine.

Ampholytic surfactants are surface-active compounds which, apart from a $C_8$-$C_{24}$ alkyl or acyl group, contain at least one free amino group and at least one —COOH— or —SO$_3$H group in the molecule and can form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each with about 8 to 24 C atoms in the alkyl group. Typical examples of amphoteric or zwitterionic surfactants are alkylbetaines, alkylamidobetaines, amino-propionates, aminoglycinate, imidazoliniumbetaines and sulfobetaines.

Examples of ampholytic surfactants are N-cocosalkylaminopropionate, cocosacylaminoethylaminopropionate and $C_{12}$-$C_{18}$-acyl sarcosine.

In addition, the products may also contain at least one cationic surfactant. Cationic surfactants are surfactants, i.e., surface-active compounds, each with one or more positive charges. Cationic surfactants contain only positive charges. Usually, these surfactants are composed of a hydrophobic part and a hydrophilic head group, the hydrophobic part usually including a hydrocarbon backbone (e.g., including one or two linear or branched alkyl chains) and the positive charge(s) being in the hydrophilic head group. Examples of cationic surfactants are quaternary ammonium compounds which, as hydrophobic radicals, may carry one or two alkyl chains with a chain length of 8 to 28 C atoms, quaternary phosphonium salts substituted with one or more alkyl chains with a chain length of 8 to 28 C atoms or tertiary sulfonium salts.

Furthermore, the cationic charge can also be part of a heterocyclic ring (e.g., an imidazolium ring or a pyridinium ring) in the form of an onium structure. In addition to the functional unit carrying the cationic charge, the cationic surfactant may also contain other uncharged functional groups, as is the case for example with esterquats. The cationic surfactants are used in a total quantity of 0.1 to 45 wt. %, preferably 1 to 30 wt. % and most preferably 1 to 15 wt. %—based on the total weight of the respective agent.

Furthermore, the means as contemplated herein may also contain at least one anionic surfactant. Anionic surfactants are surface-active agents with exclusively anionic charges (neutralized by a corresponding counter cation). Examples of anionic surfactants are fatty acids, alkyl sulphates, alkyl ether sulphates and ether carboxylic acids with 12 to 20 C atoms in the alkyl group and up to 16 glycol ether groups in the molecule.

If, in principle, both anionic and cationic and/or non-ionic surfactants can be used in the composition as contemplated herein, it has proved particularly preferable not to use further ionic compounds or to use them only in small quantities. In other words, a particularly strong improvement in color intensity could be achieved when the agent was a predominantly non-ionic base and therefore contained cationic and anionic surfactants either not at all or only in very small amounts. For this reason, it has been found to be particularly preferable if the total content of all anionic surfactants contained in the formulation is below 0.1% by weight. Furthermore, it has been found to be particularly preferable if the total content of all cationic surfactants contained in the agent is below 0.1% by weight. The amount of catalytic or anionic surfactant is related to the total weight of the product.

In another very particularly preferred embodiment, a means as contemplated herein is exemplified in that—in relation to the total weight of the means the total content of all anionic surfactants contained in the composition is below 0.1% by weight, and the total content of all cationic surfactants contained in the composition is below 0.1% by weight.

The compositions may also contain other active ingredients, auxiliaries and additives, such as solvents, structurants such as glucose, maleic acid and lactic acid, hair-conditioning compounds such as phospholipids, for example lecithin and cephalins; perfume oils, dimethyl isosorbide and cyclodextrins; fiber structure-improving active ingredients, in particular mono-, di- and oligosaccharides such as glucose, galactose, fructose, fructose and lactose; dyes for coloring the product; anti-dandruff active ingredients such as piroctone olamine, zinc omadine and climbazole; amino acids and oligopeptides; protein hydrolysates on an animal and/or vegetable basis, as well as in the form of their fatty acid condensation products or optionally anionically or cationically modified derivatives; vegetable oils; light stabilizers and UV blockers; active ingredients such as panthenol, pantothenic acid, pantolactone, allantoin, pyrrolidinonecarboxylic acids and their salts, and bisabolol; polyphenols, in particular hydroxy cinnamic acids, 6,7-dihydroxycoumarins, hydroxybenzoic acids, catechins, tannins, leucoanthocyanidins, anthocyanidins, flavanones, flavones and flavonols; Ceramides or pseudoceramides; vitamins, provitamins and vitamin precursors; plant extracts; fats and waxes such as fatty alcohols, beeswax, montan wax and kerosenes; Swelling and penetrating agents such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate as well as PEG-3-distearate; and blowing agents such as propane-butane mixtures, $N_2O$, dimethyl ether, $CO_2$ and air.

The selection of these other substances will be made by the specialist according to the desired properties of the agents. Regarding other optional components and the quantities of these components used, explicit reference is made to the relevant manuals known to the specialist. The additional active ingredients and auxiliary substances are preferably used in the preparations as contemplated herein in quantities of 0.0001 to 25 wt. % each, 0.0005 to 15 wt. %, based on the total weight of the respective agent.

Agent pH Value

The pH value of the agent as contemplated herein is preferably adjusted to a neutral to alkaline pH. Most preferably, the agent has an alkaline pH value in the range of 7.0 to 11.5 preferably from 8.0 to 11.0, and most preferably from 8.5 to 10.5. Under basic conditions, the amino-functionalized silicone polymer (a1) can be dissolved or dispersed particularly well and without protonation.

Within the scope of a further preferred embodiment, an agent as contemplated herein is has a pH of from 7.0 to 11.5 preferably from 8.0 to 11.0, and particularly preferably from 8.5 to 10.5.

To adjust the desired pH, the agent (a) and/or (b) may contain at least one alkalizing agent. The pH values for the purposes of the present disclosure are pH values measured at a temperature of 22° C.

As alkalizing agents, the agents may contain, for example, ammonia, alkanolamines and/or basic amino acids.

The alkanolamines which can be used in the composition of the invention are preferably selected from primary amines having a $C_2$-$C_6$ alkyl base which carries at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

Alkanolamines particularly preferred as contemplated herein are selected from 2-aminoethan-1-ol and/or 2-amino-2-methylpropan-1-ol. A particularly preferred embodiment is therefore exemplified in that the agent as contemplated herein contains an alkanolamine selected from 2-aminoethan-1-ol and/or 2-amino-2-methylpropan-1-ol as alkalizing agent.

A particularly preferred embodiment is therefore exemplified in that the agent as contemplated herein contains an alkanolamine selected from 2-aminoethan-1-ol and/or 2-amino-2-methylpropan-1-ol as alkalizing agent. Preferred amino acids are amino carboxylic acids, especially α-(alpha)-amino carboxylic acids and ω-amino carboxylic acids, whereby α-amino carboxylic acids are particularly preferred.

As contemplated herein, basic amino acids are those amino acids which have an isoelectric point pI of greater than 7.0.

Basic α-amino carboxylic acids contain at least one asymmetric carbon atom. In the context of the present disclosure, both possible enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine and histidine, especially preferably arginine and lysine. In another particularly preferred embodiment, an agent as contemplated herein is therefore exemplified in that the alkalizing agent is a basic amino acid from the group arginine, lysine, ornithine and/or histidine.

In addition, the product may contain other alkalizing agents, especially inorganic alkalizing agents. Inorganic alkalizing agents usable as contemplated herein are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Particularly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-Amino-2-methylpropan-2-ol, 3-aminopropan-1,2-diol, 2-amino-2-methylpropan-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

In another very particularly preferred embodiment, a process as contemplated herein is exemplified in that the colorant (a) comprises at least one alkalizing agent selected from the group including ammonia, 2-aminoethan-1-ol (monoethanolamine), 3-aminopropan-1-ol, 4-aminobutan-1-ol, 5-aminopentan-2-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Process for Dyeing Keratin Material

The agents described above can be excellently used in processes for dyeing keratinous material, especially human hair.

A second object of the present disclosure is therefore a method for coloring keratinous material, in particular human hair, comprising the following steps:
(1) Application of a coloring agent to the keratinous material, wherein the coloring agent is an agent as disclosed in detail in the description of the first subject matter of the invention,
(2) Exposure of the colorant to the keratinous material and
(3) Rinse out the dye with water.

In step (1) of the process as contemplated herein, the agent of the first invention is applied to the keratinous material, which is most preferably human hair.

In step (2) of the process as contemplated herein, the agent is then allowed to act on the keratinous material after its application. In this context, different exposure times of, for example, 30 seconds to 60 minutes are conceivable.

However, a major advantage of the dyeing system as contemplated herein is that an intensive color result can be achieved even in very short periods after short exposure times. For this reason, it is advantageous if the application mixture remains on the keratin material only for comparatively short periods of time after its application, from 30 seconds to 15 minutes, preferably from 30 seconds to 10 minutes, and particularly preferably from 1 to 5 minutes.

In a further preferred embodiment, a method as contemplated herein is.
exemplified by:
(2) Exposure of the colorant to the keratinous material for a period ranging from 30 seconds to 15 minutes, preferably from 30 seconds to 10 minutes, and most preferably from 1 to 5 minutes.

Finally, following the action of the application mixture on the keratin material, it is rinsed with water in step (3) of the process.

Here, in one embodiment, the application mixture can be washed out with water only, i.e., without the aid of an after-treatment agent or a shampoo. The use of a post-treatment agent or conditioner in step (6) is also conceivable in principle.

However, to solve the task as contemplated herein and to increase the convenience of use, it has proved particularly preferable to rinse the agent in step (3) exclusively with water without the aid of a further after-treatment agent, shampoo or conditioner.

In a further preferred embodiment, a method as contemplated herein is.
exemplified by:
(3) Rinse out the dye with water only.

Concerning the further preferred embodiments of the method as contemplated herein, mutatis mutantis what has been said about the means as contemplated herein applies.

EXAMPLES

1. Formulations
The following formulations were prepared (all data in wt. % unless otherwise stated):

| Colorants | (V1) | (E1) |
|---|---|---|
| Cetyl alcohol | 3.6 | 3.6 |
| Stearyl alcohol | 2.1 | 2.1 |
| Paraffinum Liquidum | 2.1 | 2.1 |
| Ceteareth-30 (Cetearyl alcohol, ethoxylated 30 EO) | 1.2 | 1.2 |
| Brij S 100 PA SG (stearyl alcohol, ethoylated 100 EO, Croda) | 0.6 | 0.6 |
| Cutina GMS V (INCI: Glyceryl stearate, glyceol mono/dipalmitate/stearate) CAS No. 85251-77-0 | 0.6 | 0.6 |
| 1.2-propanediol | 6.3 | 6.3 |
| Lavanya Zuni (organic pigment, Neelikon Red, 111P0200, CI 12490) | 0.3 | 0.3 |
| Dow Corning 2-8566 (Siloxanes and Silicones, 3-[(2-Aminoethyl)amino]-2-methylpropyl Me, Di-Me-Siloxane" | 2.5 | 2.5 |
| Benzyl alcohol | — | 0.4 |
| Water | ad 100 | ad 100 |

2. Application

The agent (E1) was applied to hair strands (Kerling, Euronatural hair white, liquor ratio: 1 g of colorant (E1) per g of hair strand) applied. The agent was left to act for three minutes. Subsequently, the hair strand was thoroughly washed (1 minute) with water, dried and then colorimetrically measured with a colorimeter from Datacolor, type Spectraflash 450.

As a comparison, the comparative formulation V1 was applied to hair strands (Kerling, Euronatural hair white, liquor ratio: 1 g of colorant (V1) per g of hair strand) applied and left to act for three minutes. Subsequently, these hair strands were also thoroughly washed (1 minute) with water, dried and colorimetrically measured.

The dE value used to evaluate the different color intensities is derived from the L*a*b* colorimetric values measured on the respective strand part as follows:

$$dE=[(L_i-L_0)^2+(a_i-a_0)^2+(b_i-b_0)]^{1/2}$$

$L_0$, $a_0$ and $b_0$=measured values of the staining obtained with the comparative formulation.
$L_i$, $a_i$ and $b_i$=measured values of the coloration obtained with the formulation as contemplated herein.

The chroma of a coloration is calculated according to the formula $$C=\sqrt{a^2+b^2}$$

The larger the C-value, the higher the chromaticity of a coloration.

| Agent | L | a | b | Chroma C | dE |
|---|---|---|---|---|---|
| Comparison (V1) | 51.01 | 36.13 | 13.56 | 38.59 | 6.5 |
| Invention (E1) | 47.50 | 41.58 | 13.64 | 43.76 | |

The color difference between the coloration obtained with the comparative formulation and the coloration obtained with the formulation as contemplated herein was 6.5.

The coloration obtained with the formulation as contemplated herein was darker or more intense (lower L value) and possessed a higher chroma (higher chroma, higher C value).

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An agent for dyeing keratinous material, comprising
   (a1) at least one amino-functionalized silicone polymer,
   (a2) at least one color-imparting compound,
   (a3) at least one preservative, wherein the at least one preservative comprises benzyl alcohol (a3), and
   (a4) at least one fat component.

2. The agent according to claim 1, wherein the at least one amino-functionalized silicone polymer (a1) has at least one secondary amino group.

3. The agent according to claim 1, wherein the at least one amino-functionalized silicone polymer (a1) comprises at least one structural unit of the formula (Si amino),

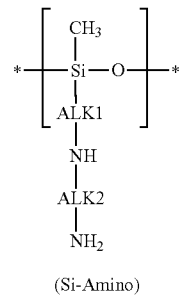

(Si-Amino)

where ALK1 and ALK2 independently represent a linear or branched $C_1$-$C_{20}$ divalent alkylene group.

4. The agent according to claim 1, wherein the at least one amino-functionalized silicone polymer (a1) comprises structural units of the formula (Si-I) and of the formula (Si-II)

(Si-I)

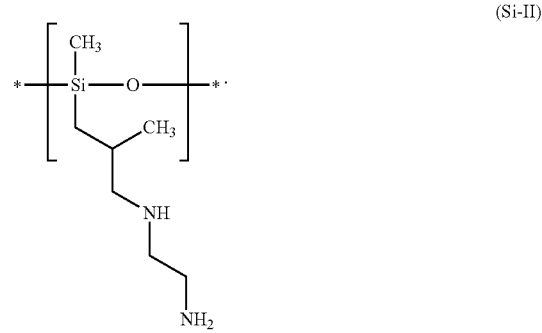

(Si-II)

5. The agent according to claim 1 wherein, based on the total weight of the agent, the at least one amino-functionalized silicone polymer comprises one or more amino-functionalized silicone polymers (a1) in a total amount of from 0.1 to 8.0% by weight.

6. The agent according to claim 1, wherein the at least one colorant compound (a2) is selected from the group of pigments, direct dyes, photochromic dyes and thermochromic dyes.

7. The agent according to claim 1, wherein the at least one colorant compound (a2) is selected from the group of colored metal oxides, metal hydroxides, metal oxide hydrates, silicates, metal sulfides, complex metal cyanides, metal sulfates, bronze pigments, colored mica pigments coated with at least one metal oxide, colored mica pigments coated with at least one metal oxychloride, mica-based pigments coated with at least one metal oxide, and mica-based pigments coated with at least one metal oxychloride.

8. The agent according to claim 1, wherein the at least one coloring compound (a2) is selected from the group of carmine, quinacridone, phthalocyanine, sorghum, blue pigments with the color index numbers C1 42090, CI 69800, CI 69825, CI 73000, CI 74100, CI 74160, yellow pigments with the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, and red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, and CI 75470.

9. The agent according to claim 1, wherein, based on the total weight of the agent, the at least one color-imparting compound comprises one or more pigments (a2) in a total amount of 0.01 to 10.0% by weight.

10. The agent according to claim 1, wherein based on the total weight of the agent, the at least one preservative comprises one or more preservatives (a3) in a total amount of from 0.1 to 1.5% by weight.

11. The agent according to claim 1, wherein, based on the total weight of the agent, the at least one preservative comprises one or more preservatives (a3) in a total amount of from 0.01 to 5.0% by weight.

12. The agent according to claim 1, wherein, based on the total weight of the agent, the at least one preservative comprises from 0.1 to 1.5% by weight of benzyl alcohol (a3).

13. The agent according to claim 1, wherein the at least one fat component comprises one or more fat constituents from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons.

14. The agent according to claim 1, wherein the at least one fat component comprises one or more $C_{12}$-$C_{30}$-fatty alcohols (a4) selected from the group of dodecan-1-ol, tetradecan-1-ol, hexadecan-1-ol, octadecan-1-ol, eicosan-1-ol, heneicosan-1-ol, docosan-1-ol, (9Z)-octadec-9-en-1-ol, (9E)-Octadec-9-en-1-ol, (9Z,12Z)-Octadeca-9,12-dien-1-ol, (9Z,12Z,15Z)-Octadeca-9,12,15-trien-1-ol, (9Z)-Eicos-9-en-1-ol, (5Z,8Z,11Z,14Z)-Eicosa-5,8,11,14-tetraen-1-ol, (13Z)-docos-13-en-1-ol), (13E)-docosen-1-ol), 2-octyl-dodecanol, 2-hexyl-dodecanol, and/or 2-butyl-dodecanol.

15. The agent according to claim 1, wherein the agent further comprises at least one non-ionic surfactant (a5) of the formula (T-I),

wherein
Ra is a saturated or unsaturated, unbranched or branched $C_8$-$C_{24}$ alkyl group, and
n is an integer from 80 to 120.

16. The agent according to claim 1, wherein the agent further comprises at least one non-ionic surfactant (a5) of the formula (T-II),

wherein
Rb represents a saturated or unsaturated, unbranched or branched $C_8$-$C_{24}$ alkyl group, and
m an integer from 10 to 40.

17. The agent according to claim 1, wherein the agent comprises anionic polymers and/or cationic polymers, and wherein, based on the total weight of the agent,
the total content of all anionic polymers included in the agent is less than 0.1% by weight, and
the total content of all cationic polymers included in the agent is less than 0.1% by weight.

18. The agent according to claim 1, wherein the agent comprises anionic surfactants and/or cationic surfactants, and wherein, based on the total weight of the agent,
the total content of all anionic surfactants included in the agent is less than 0.1% by weight, and
the total content of all cationic surfactants included in the agent is less than 0.1% by weight.

19. The agent according to claim 1, further comprising water, and wherein the agent has a pH of from 7.0 to 11.5.

20. A method for dyeing keratinous material comprising the following steps:
(1) applying a colorant according to claim 1 to the keratinous material,
(2) reacting the dyeing agent with the keratinous material, and
(3) rinsing the dyeing agent with water.

* * * * *

UNITED STATES PATENT AND TRADEMARK OFFICE
CERTIFICATE OF CORRECTION

PATENT NO. : 11,878,071 B2
APPLICATION NO. : 17/620093
DATED : January 23, 2024
INVENTOR(S) : Constanze Kruck et al.

It is certified that error appears in the above-identified patent and that said Letters Patent is hereby corrected as shown below:

In the Specification

Column 6, Line 49 change "$C_1$-4" to --C1-4--
Column 7, Line 52 change "isopropyl, isopropyl" to --isopropyl--
Column 8, Line 16 change "$CH_2CH_2CH_2NHCH_2CH_2NH2$" to --$CH_2CH_2CH_2NHCH_2CH_2NH_2$--
Column 14, Line 52-53 change "isoindolinone, isoindolinone" to --isoindolinone--
Column 17, Line 17 change "COLIPA no B001" to --COLIPA n° B001--
Column 17, Line 18 change "COLIPA no: C54" to --COLIPA n°: C 54--
Column 17, Line 18 change "D&C Yellow No 10" to --D&C Yellow N° 10--
Column 17, Line 20 change "COLIPA no C 29" to --COLIPA n° C 29--
Column 17, Line 26 change "COLIPA no C015" to --COLIPA n° C015--
Column 17, Line 35 change "(CI C.I. 18065)" to --CI 18065--
Column 17, Line 38-39 change "Red no 106" to --Red n° 106--
Column 17, Line 40-41 change "COLIPA no C53" to --COLIPA n° C53--
Column 17, Line 43-44 change "Violet no 2" to --Violet n° 2--
Column 17, Line 44 change "COLIPA no C063" to --COLIPA n° C063--
Column 17, Line 55 change "Black no 401" to --Black n° 401--
Column 17, Line 57 change "COLIPA no B15" to --COLIPA n° B15--
Column 24, Line 30-31 change "phenyl-O-hydroxypropyl ether" to --phenyl-β-hydroxypropyl ether--
Column 32, Line 22 change "number pin" to --number p--
Column 35, Line 59 change "$C_{12}$-22" to --C12-22--
Column 38, Line 12 change "fructose, fructose" to --fructose--
Column 38, Line 22 change "hydroxy cinnamic" to --hydroxycinnamic--

Signed and Sealed this
Twenty-second Day of April, 2025

Coke Morgan Stewart
*Acting Director of the United States Patent and Trademark Office*